United States Patent [19]
Jacobs et al.

[11] Patent Number: 6,090,811
[45] Date of Patent: *Jul. 18, 2000

[54] ANTI-NEUROGENIC INFLAMMATORY COMPOUNDS AND COMPOSITIONS AND METHODS OF USE THEREOF

[75] Inventors: Robert S. Jacobs, Santa Barbara, Calif.; Shirley A. Pomponi, Fort Pierce, Fla.; Sarath P. Gunasekera, Vero Beach, Fla.; Amy E. Wright, Fort Pierce, Fla.

[73] Assignees: Harbor Branch Oceanographic Institution, Inc., Fort Pierce, Fla.; Regents of the Univ. of California, Oakland, Calif.

[ * ] Notice: This patent is subject to a terminal disclaimer.

[21] Appl. No.: 09/356,282

[22] Filed: Jul. 16, 1999

Related U.S. Application Data

[63] Continuation of application No. 08/961,475, Oct. 31, 1997, Pat. No. 5,955,462
[60] Provisional application No. 60/030,261, Oct. 31, 1996.

[51] Int. Cl.$^7$ .................. A61K 31/40; A61K 31/415; A61K 31/495
[52] U.S. Cl. ................... 514/254; 514/397; 514/402; 514/497
[58] Field of Search ..................... 514/254, 397, 514/402, 497

[56] References Cited

U.S. PATENT DOCUMENTS

| | | |
|---|---|---|
| 4,866,084 | 9/1989 | Gunasekera et al. . |
| 4,895,844 | 1/1990 | Komoto et al. . |
| 4,970,226 | 11/1990 | Sun et al. . |
| 5,290,777 | 3/1994 | McConnell et al. . |
| 5,464,835 | 11/1995 | McConnell et al. . |

FOREIGN PATENT DOCUMENTS

| | | |
|---|---|---|
| 0768301 | 4/1997 | European Pat. Off. . |
| 9404494 | 3/1994 | WIPO . |
| 9419343 | 9/1994 | WIPO . |
| 9532966 | 12/1995 | WIPO . |
| 9533744 | 12/1995 | WIPO . |

OTHER PUBLICATIONS

Faulkner, D.J. (1984) "Marine Natural Products: Metabolites of Marine Invertebrates" *Natural Products Reports* 1:551–598.
Faulkner, D.J. (1986) "Marine Natural Products" *Natural Products Resources* 3:1–33.
Faulkner, D.J. (1987) "Marine Natural Products" *Natural Products Reports* 4(5):539–576.
Uemura, D. et al. (1985) "Norhalichondrin A: An Antitumor Polyether Macrolide from a Marine Sponge" *J. Am. Chem. Soc.* 107:4796–4798.
Moquin, D., M. Guyot (1984) "Grossularine, A Novel Indole Derivative from the Marine Tunicate, *Dendrodoa grossularia*" *Tetrahedron Letters* 25(44):5047–5048.

*Primary Examiner*—Keith D. MacMillan
*Attorney, Agent, or Firm*—Saliwanchik, Lloyd & Saliwanchik

[57] ABSTRACT

A novel use for the class of biologically active bis-heterocyclic, e.g., bis-indole alkaloid compounds, which have been named topsentins, bromotopsentins, homocarbonyltopsentins, nortopsentins, hamacanthins, bis-indole ethylamines, or dragmacidins, pharmaceutical compositions containing the compounds, methods of producing the compounds, and methods of using the compounds are disclosed. Specifically, the novel utility pertains to the anti-neurogenic inflammatory properties exhibited by the bis-indole compounds and their analogs.

21 Claims, 7 Drawing Sheets

ANTI-NEUROGENIC INFLAMMATORY COMPOUNDS AND COMPOSITIONS AND METHODS OF USE THEREOF

CROSS-REFERENCE TO A RELATED APPLICATION

This application is a continuation of patent application Ser. No. 08/961,475, filed Oct. 31, 1997, U.S. Pat. No. 5,955,462 which claims benefit to U.S. provisional Ser. No. 60/030,261 filed Oct. 31, 1996.

This invention was made with Government support under NOAA Grant No. NA36RG0537. The Government has certain rights in this invention.

FIELD OF THE INVENTION

This application relates to compounds which are used as anti-inflammatory agents and compositions containing such compounds as active ingredients. More particularly, the invention concerns a novel use of biologically active bis-heterocyclic compounds, e.g., bis-indoles, pharmaceutical compositions containing these compounds, and methods of producing the compounds. The novel use of the compounds relates to the anti-neurogenic inflammatory properties of the disclosed bis-heterocyclic compounds, which include the bis-indoles known as topsentins, bromotopsentins, nortopsentins, dragmacidins, hamacanthins, bis-indole ethylamines, and their salts, analogs and derivatives.

BACKGROUND OF THE INVENTION

The prevention and control of inflammation is of prime importance to man, and much research has been devoted to development of compounds having anti-inflammatory properties. Certain methods and chemical compositions have been developed which aid in inhibiting or controlling inflammation, but additional anti-inflammatory methods and compositions are needed.

It has been found that some natural products and organisms are potential sources for chemical molecules having useful biological activity of great diversity. Marine sponges have proved to be such a source, and a number of publications have issued disclosing organic compounds derived from marine sponges. Such publications include Scheuer, P. J., Ed. (1978–1983) *Marine Natural Products, Chemical and Biological Perspectives,* Academic Press, New York; Faulkner, D. (1995) *J. Nat. Prod. Rep.* 12:223–269; (1994) 11:355–394; (1993) 10:497–539; (1992) 9:323–364; (1991) 8:97–147; (1990) 7:269–309; (1988) 5:613–663; (1987) 4:539–576; (1986) 3:1–33; (1984) 1:551–598; and Uemura, D., K. Takahashi, T. Yamamoto, C. Katayama, J. Tanaka, Y. Okumura, Y. Hirata (1985) *J. Am. Chem. Soc.* 107:4796–4798.

Indole compounds of marine origin have also been described in Moquin, C., M. Guyot (1984) *Tetrahedron Letters* 25(44):5047–5048 and Norton, R. S., R. J. Wells (1982) J. Am. Chem. Soc. 104(13):3628–3635.

Utilizing sponges as a source material and supplemented by novel synthetic production methods, new classes of biologically active compounds and new pharmaceutical compositions useful as antitumor and antiviral agents have been provided to the art. For example, bis-heterocyclic compounds such as bis-indoles have been previously described as having antimicrobial, antitumor, or antiviral activity. Specifically, the bis-indole compounds known as top sentins are disclosed in U.S. Pat. No. 4,866,084. Dragmacidinand its related compounds isolated from the marine sponge of the Dragmacidon sp. are disclosed in U.S. Pat. No. 4,895,844. Similarly, the nortopsentins have been disclosed in U.S. Pat. No. 4,970,226. These patents are herein incorporated by reference. These compounds, as well as the homocarbonyltopsentins and hamacanthins, have also been described as having inhibitory activity against cellular inflammatory responses. See U.S. Pat. Nos. 5,290,777 and 5,464,835 which are also hereby incorporated by reference. The present invention provides a novel utility for these and related compounds, namely as anti-neurogenic inflammatory compositions.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The objects of the invention are accomplished by the provision of a novel utility for the class of biologically active bis-heterocyclic compounds that have a general structure according to the formula:

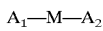

$$A_1-M-A_2$$

wherein each of $A_1$ and $A_2$ is a heterocycle; and M is a core moiety linking the heterocycles, $A_1$ and $A_2$. Typically, the compound comprises an indole as the $A_1$ and $A_2$ moieties. Thus, the compound can be a bis-indole. The bis-indoles can be topsentins, nortopsentins, dragmacidins, hamacanthins, bis-indole ethylamines, and salts, analogs, or derivatives thereof. Other compounds of the subject invention can comprise heterocycles such as pyridyl or purine as the $A_1$ and $A_2$ moieties, thus forming, for example, bis-pyridine or bis-purine compounds.

As embodied and fully described herein, the invention also comprises pharmaceutical compositions, e.g., anti-neurogenic inflammatory compositions, containing as an active ingredient an effective amount, preferably between about 0.1 to 45%, especially 1 to 25%, by weight based on the total weight of the composition, of one or more compounds according to the formulas expressed above and a non-toxic, pharmaceutically acceptable carrier or diluent. In addition, a pharmaceutical composition can comprise at least one of the subject bis-indole compounds and a second component comprising at least one other active compound. Such other active compounds include, but are not limited to, anti-inflammatory compounds, for example, steroidal compounds, including hydrocortisone and the like; or non-steroidal anti-inflammatories, including acetylsalicylic acid (aspirin), ibuprofen, acetaminophen, indomethacin, and the like. The second active ingredient can include antiviral, antibacterial, antifungal or other antimicrobial compounds, or antitumor compounds, as well.

As embodied and fully described herein, the invention comprises processes for the production of compounds and compositions of the invention and novel methods of use thereof, e.g., methods of inhibiting a neurogenic inflammatory response in an animal.

In accordance with the invention, methods for inhibiting inflammation comprise administering to the animal in need of such treatment an effective amount of the pharmaceutical compositions of the invention.

DETAILED DISCLOSURE OF THE INVENTION

Figure 1:
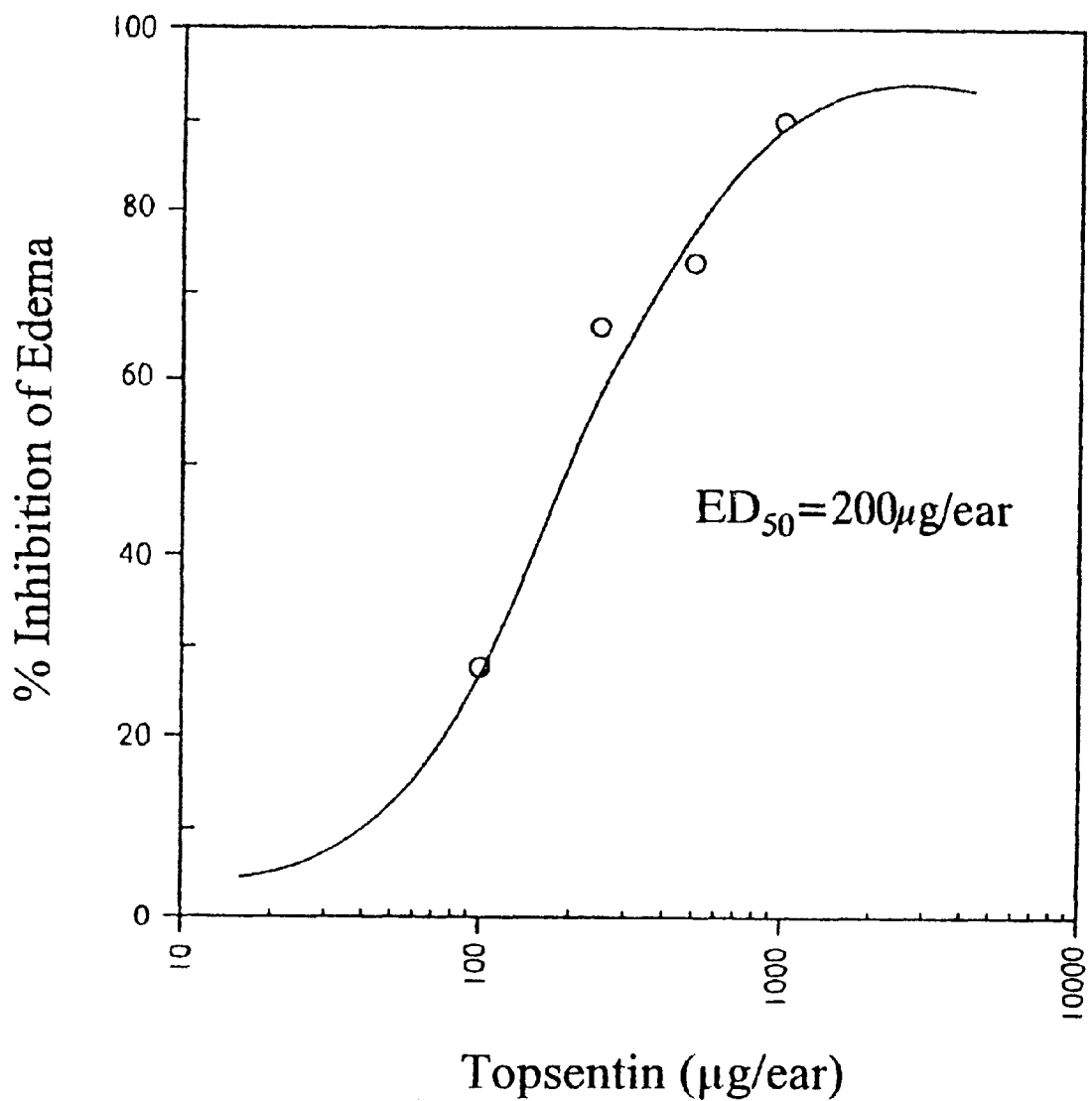
FIG. 1 shows a typical log dose response curve of a bis-heterocycle of the subject invention (topsentin) illustrating its inhibition of capsaicin-induced edema in a mouse ear model.

The subject invention pertains to a novel use as an anti-inflammatory agent of bis-heterocyclic compounds and compositions comprising the bis-heterocyclic compounds. Surprisingly, the bis-heterocycle compounds of the subject invention can be highly effective in inhibiting neurogenic inflammation.

The subject compounds comprise a chemical of the general formula:

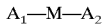

wherein each of $A_1$ and $A_2$ is a heterocycle; and M is a core moiety linking the heterocycles, $A_1$ and $A_2$. These heterocycles, $A_1$ and $A_2$, can be the same or different, but are preferably the same. The heterocycles $A_1$ and $A_2$ can be indole, pyridine, pyrimidine, purine, pyrrole, furan, theophene, imidazole, benzimidazole, oxazole, thiazole, pyrazole, 3-pyrroline, pyrrolidine, quinolone, isoquinolone, carbazole, cyclic anhydride, cyclic imide, lactone, and the like. The heterocycles can be linked to the core group at any position on the heterocyclic ring. When the core moiety is a ring structure, the heterocyclic rings $A_1$ and $A_2$ can be linked thereto at any position on the core moiety. The specific bond position for any particular compound of the subject invention would be apparent to an ordinarily skilled artisan having the benefit of the instant disclosure. Substitutions and additions to the heterocycles are also readily recognized by those persons of ordinary skill in the organic chemical arts.

The core moiety, M, linking the heterocycles, can be a cyclic or acyclic group comprising at least three atoms. The core moiety can comprise an acyclic chain having C, H, N, O, or S atoms. For example, M can be the core group

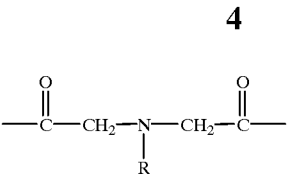

wherein R is a C1–C8 alkyl or alkoxyl group. A condensation reaction with this group yields the heterocycle:

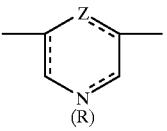

wherein $Z=CH$, $CH_2$, N, NH, O, or S; and $R=C1–C8$ alkyl or alkoxyl group. Other heterocycles which can be used as the core group for compounds used in the subject invention are known to, and easily recognized by, those of ordinary skill in the art. As with the heterocycles discussed above, ordinarily skilled chemists would recognize that when the core moiety is a cyclic structure, the bonds to the heterocycles can be at any position of the core ring. These other core group heterocycles include:

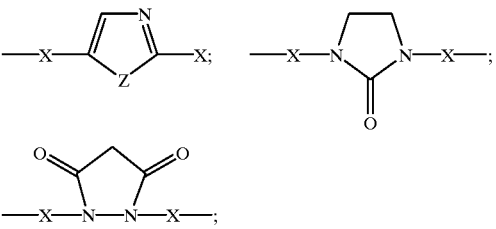

and the like, wherein X can be present or absent and can be an organic moiety, e.g., any lower alkyl or lower alkoxyl, or an inorganic molecule which can bond to the core group and the bis-heterocycles of the compound; and Z can be $CH_2$, NH, O, or S.

A preferred embodiment of the subject invention is a bis-indole compound, wherein the indoles can be linked to the core group at the 2- or 3- positions of the indoles. One preferred embodiment includes a bis-indole compound wherein both indoles are linked to the core group at the 3-position. This preferred embodiment is shown below as the structure:

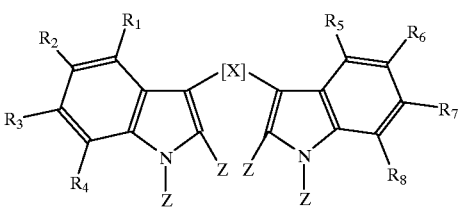

wherein X=an acyclic or a heterocyclic moiety selected from the group consisting of:

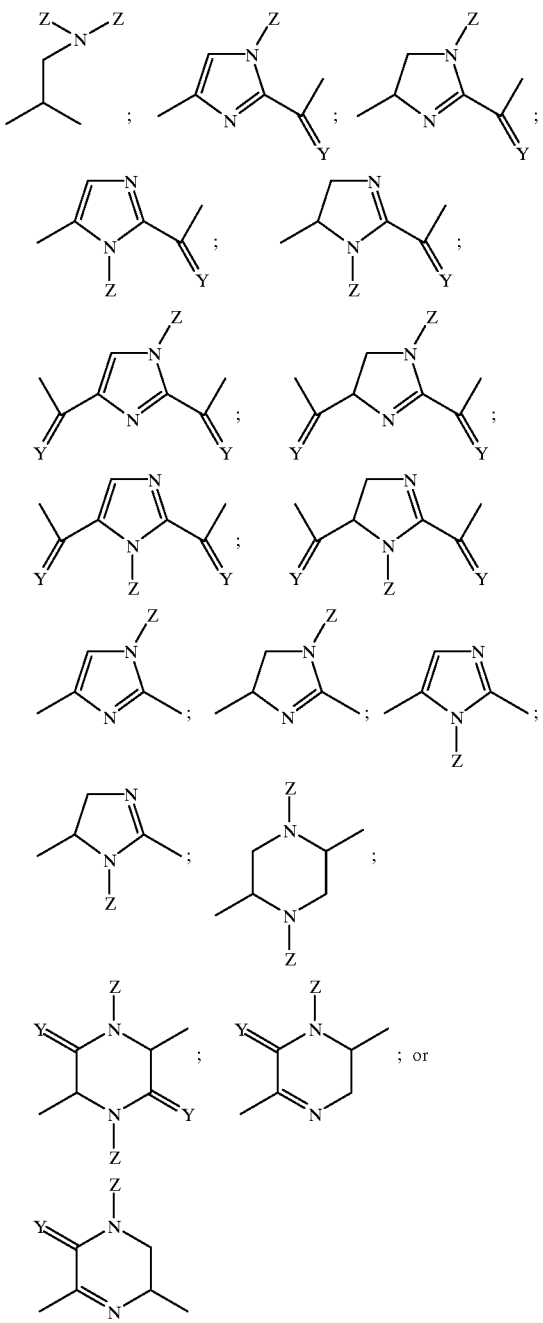

$R_{1-8}$ are the same or different selected from —H, —OH, halogen, —R, —OR, —OCOR, —OA, NHZ, NZZ (wherein the Zs can be the same or different), or $NH_2$;

Y is the single group=O, or the single group=NZ, or two groups, same or different, selected from —H, —OH, —OR, —OCOR, NHZ, NZZ (wherein the Zs can be the same or different), or $NH_2$;

Z is independently selected from the group consisting of —H, —R, —OH, and —COR;

R is C1–8 alkyl or C1–8 alkoxyl, mesyl, or tosyl; and A is —R-phenyl.

A preferred group of compounds of the invention are those of the formula:

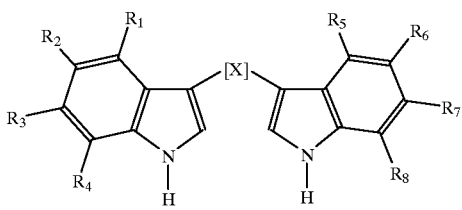

wherein X=

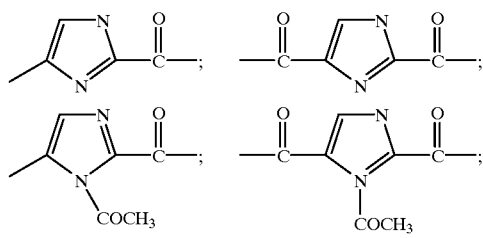

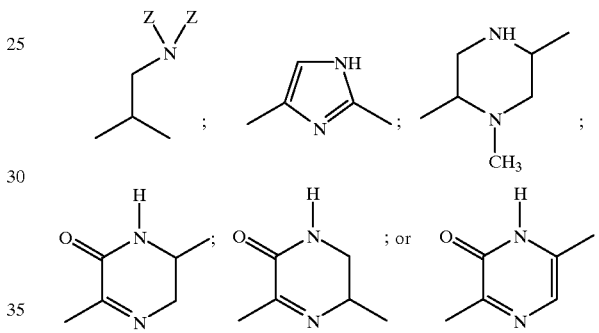

and wherein $R_1$, $R_3$, $R_4$, $R_5$, $R_7$ and $R_8$ are —H while $R_2$ and $R_6$ are independently —H, —OH, halogen, —R, —OR, —OCOR, $NH_2$, NHZ, NZZ (wherein the Zs can be the same or different), or —OA; or $R_1$, $R_2$, $R_4$, $R_5$, $R_6$ and $R_8$ are —H while $R_3$ and $R_7$ are independently —H, —OH, halogen, —R, —OR, —OCOR, $NH_2$, NHZ, NZZ (wherein the Zs can be the same or different), or —OA; Z is independently selected from the group consisting of —H, —R, —OH, and —COR; R is C1–5 alkyl, and A is —R-phenyl; or $R_1$, $R_2$, $R_3$, $R_4$, $R_6$, $R_7$ and $R_8$ are independently —H, —OH, halogen, —R, —OR, —OCOR, or —OA are H and $R_5$ is C1–5 alkyl-1-(2-amino imidazole) ethyl.

Particularly preferred compounds of the invention are those of the formulae:

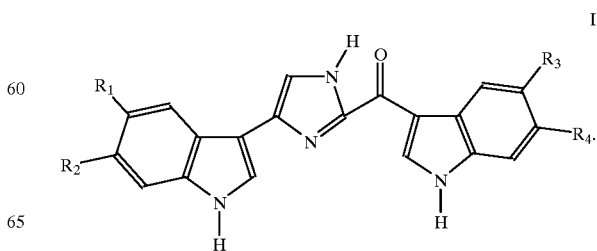

I

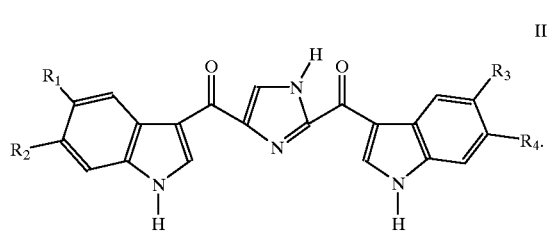
II
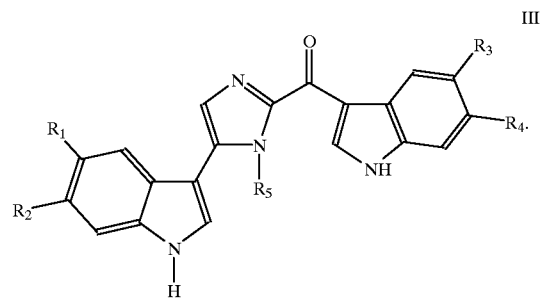
III
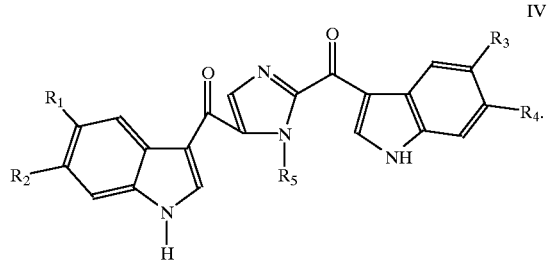
IV
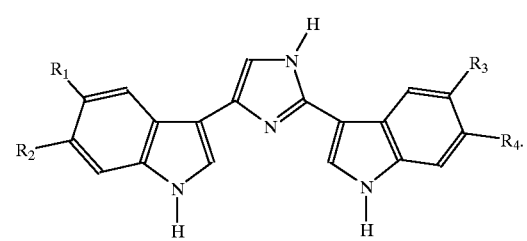
V
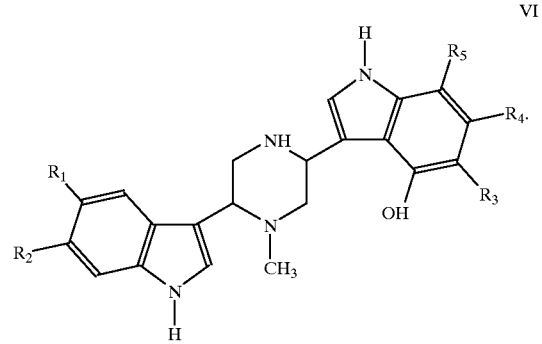
VI
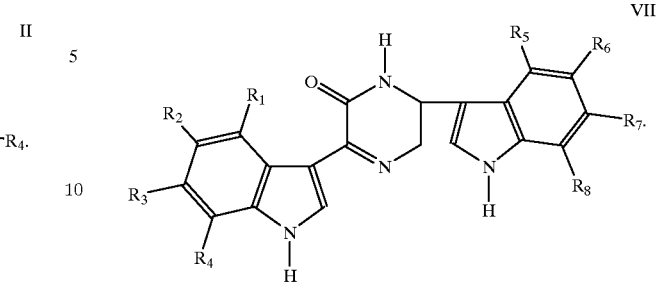
VII
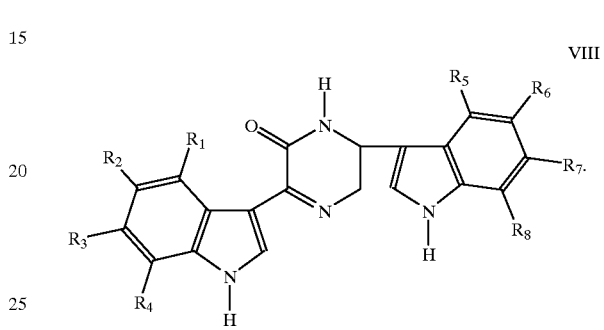
VIII
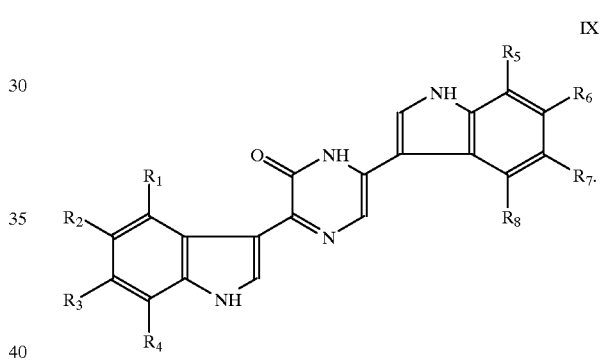
IX
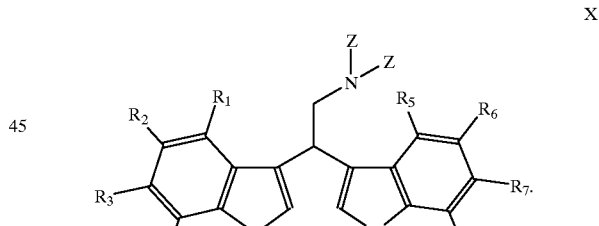
X
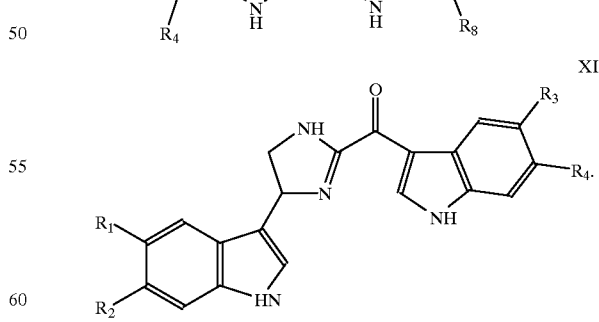
XI
wherein:

| | | |
|---|---|---|
| I(a): | $R_1$, $R_2$, $R_3$ = H; $R_4$ = OH | (Topsentin) |
| I(b): | $R_1$, $R_3$ = H; $R_2$ = Br; $R_4$ = OH | (Bromotopsentin) |
| I(c): | $R_1$, $R_3$, $R_4$ = H; $R_2$ = OH | (Isotopsentin) |
| I(d): | $R_1$, $R_3$ = H; $R_2$, $R_4$ = OH | (Hydroxytopsentin) |
| I(e): | $R_1$, $R_2$, $R_3$, $R_4$ = H | (Deoxytopsentin) |
| I(f): | $R_1$, $R_2$, $R_4$ = H; $R_3$ = OH | (Neotopsentin) |
| I(g): | $R_2$, $R_3$, $R_4$ = H; $R_1$ = OH | (Neoisotopsentin) |
| I(h): | $R_1$, $R_3$ = OH; $R_2$, $R_4$ = H | (Neohydroxytopsentin) |
| I(i): | $R_1$ = $R_3$ = H, $R_2$ = Br, $R_4$ = O—$SO_2CH_3$ | (bromotopsentin-O-mesylate) |
| II(j): | $R_1$, $R_2$, $R_3$ = H; $R_4$ = OH | (Homocarbonyltopsentin) |
| III(k): | $R_1$, $R_2$, $R_3$, $R_5$ = H; $R_4$ = $OCOCH_3$ | (Topsentin monoacetate) |
| III(l): | $R_1$, $R_2$, $R_3$ = H; $R_4$ = $OCOCH_3$; $R_5$ = $COCH_3$ | (Topsentin diacetate) |
| IV(m): | $R_1$, $R_2$, $R_3$, $R_5$ = H; $R_4$ = $OCOCH_3$ | (Homocarbonyltopsentin monoacetate) |
| V(n): | $R_1$, $R_3$ = H; $R_2$, $R_4$ = Br | (Nortopsentin A) |
| V(o): | $R_1$, $R_2$, $R_3$ = H; $R_4$ = Br | (Nortopsentin B) |
| V(p): | $R_1$, $R_3$, $R_4$ = H; $R_2$ = Br | (Nortopsentin C) |
| VI(q): | $R_1$, $R_3$ = H; $R_2$, $R_4$, $R_5$ = Br | (Dragmacidin) |
| VII(r): | $R_1$, $R_2$, $R_4$, $R_5$, $R_6$, and $R_8$ = H; $R_3$ and $R_7$ = Br | (Hamacanthin A) |
| VIII(s): | $R_1$, $R_2$, $R_4$, $R_5$, $R_6$, and $R_8$ = H; $R_3$ and $R_7$ = Br | (Hamacanthin B) |
| IX(t): | $R_1$, $R_2$, $R_4$, $R_6$, and $R_7$ = H; $R_3$ = Br; $R_5$ = OH; and | (Dragmacidin-d) |

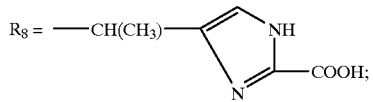

$R_8 = $ —CH(CH₃)— [imidazole ring] —COOH;

| | | |
|---|---|---|
| X(u): | $R_1$, $R_2$, $R_4$, $R_5$, $R_6$, $R_8$ = H; $R_3$ and $R_7$ = Br; Z = Z = H | (2,2-bis(6-bromoindol-3-yl)ethyl amine) |
| XI(v): | $R_1$ = $R_3$ = $R_4$ = H, $R_2$ = Br | (4,5-dihydro-6"-deoxybromotopsentin) |

Skilled chemists will be able to use procedures as disclosed herein and others to synthesize these compounds from available stock substances. In carrying out such operations, any suitable filtration, chromatographic, and other purification techniques include reversed phase (RPLC), column, vacuum flash, medium pressure (MPLC), and high performance liquid chromatography (HPLC) with a suitable column as would be known to those skilled in the art, including silica gel, Sephadex LH-20, ammonia-treated silica gel, bonded phase RP-18, RP-8, and amino ($NH_2$) columns. Such columns are eluted with suitable elements such as heptane, ethyl acetate, methylene chloride, methanol, isopropanol, acetonitrile, water, trifluoroacetic acid (TFA), and various combinations and ratios thereof.

One method of preparation for certain compounds used for the subject invention involves extraction from marine sponges of the genus Spongosorites (Phylum Porifera, Class Demospongiae, Order Halichondrida, Family Halichondriidae). Certain of the samples used in connection with this invention have been assigned to the species *Spongosorites ruetzleri* (HBOM catalog numbers 003:00112, 003:00113, 003:00114, 003:00115, 003:00116, 003:00117, 003:00118, 003:00119, 003:00120, 003:00927); other specimens represent new species of Spongosorites (HBOM Catalog Numbers 003:00594 and 003:00696). For descriptions of these samples and other Spongosorites species, refer to Diaz, M. C., Pomponi, S. A. and Van Soest, R. W. M. 1993. A systematic revision of the central West Atlantic Halichondrida (Demospongiae, Porifera), Part III: Description of valid species. Scientia Marina, 57(4): 283–306. All taxonomic voucher samples cited herein with HBOM catalog numbers are deposited in the Harbor Branch Oceanographic Museum, Fort Pierce, Fla. All voucher specimens are preserved in 70% ethanol with an expected shelf life of at least 30 years and are accessible to those skilled in the art for taxonomic identification purposes.

A current taxonomic identification of the sponge from which the compound dragmacidin (VI(1)) was extracted is: Phylum Porifera, Class Demospongiae, Order Axinellida, Family Axinellidae, Genus Dragmacidon, as disclosed in U.S. Pat. No. 4,895,844.

The hamacanthin compounds, exemplified herein as Formulae VII and VIII, were isolated from a species of Hamacantha sponge (phylum Porifera, class Demospongiae, order Poecilosclerida, family Biemnidae). See U.S. Pat. No. 5,464,835.

A novel use for the described compounds and compositions is their administration to an animal, e.g., a human, as an agent in the control of a neurogenic inflammatory response. Anti-inflammatory activity against cellular activation of specific immune cells, e.g., phorbol myristate acetate (PMA)-induced inflammation, has been described for the subject compounds. See U.S. Pat. Nos. 5,290,777 and 5,464,835, which are hereby incorporated by reference. However, it is well recognized that activity of a compound in inhibiting cellular activated inflammation (e.g., PMA-induced edema or inflammation) is not predictive or suggestive of that compound's activity in inhibiting neurogenic inflammation, e.g., capsaicin-induced or resiniferatoxin(RTX)-induced edema or inflammation. Therefore, the discovery that the subject compounds have inhibitory activity against neurogenic inflammation is unexpected and advantageous.

Neurogenic inflammation is evoked by neuropeptides released from primary afferent nerve terminals and by other secondarily released inflammatory mediators. Specifically, neurogenic inflammation can be evoked by neuropeptides, such as substance P (SP), calcitonin gene-related peptide (CGRP), vasoactive intestinal peptide (VIP), and neurokinin A (NKA), released from primary afferent C-fiber nerve terminals and histamine, secondarily released from mast cells. Dray, A. (1992). Neuropharmacological mechanisms of capsaicin and related substances. *Biochem Pharm* 44(4):611–15. For purposes of the subject invention, unless otherwise noted, the terms "inflammation" and "inflammatory response" refer to any and all such neurogenic inflammatory reactions including, but not limited to, immune-related responses and/or allergic reactions to a physical, chemical, or biological stimulus. "Anti-neurogenic inflammatory activity," as used herein, will be understood by those of ordinary skill in the art to mean biological activity inhibiting or controlling a neurogenic inflammatory response.

Anti-inflammatory activity can occur by modes of action which can include, but are not limited to, lipid-mediated inflammatory responses, e.g., (i) suppression of cellular activation of phospholipase A2, either directly (as is known for the anti-inflammatory compound, manoalide) or indirectly (as is known for the anti-inflammatory compound, hydrocortisone); (ii) by inhibiting, or controlling, cyclooxygenation of arachidonic acid, similar to the action of non-steroidal anti-inflammatory drugs; or (iii) by affecting lipooxygenase products of peroxidase reactions to arachidonic acid, or by non-lipid-mediated inflammatory responses, e.g., protease-induced inflammatory responses, and the like. In addition, it is known that capsaicin (CAP), the active constituent found in cayenne pepper, induces an acute neurogenic inflammatory response when applied topically to skin. CAP is a highly selective pain producing substance that selectively stimulates nociceptive and thermal-sensitive nerve endings in tissues by acting on a specific membrane receptor. The mode of action of capsaicin therefore differs significantly from phorbol myristate acetate (PMA)-induced inflammation. By comparison, PMA elicits its pro-inflammatory effects through cellular activation of specific immune cells, such as macrophages and neutrophils. Consequently, the pain response to PMA develops more slowly than the immediate, but transient, pain response to capsaicin.

The compounds and compositions of the subject invention advantageously can block the nociceptive (CAP-induced) inflammatory pathway, thereby providing a method for inhibiting neurogenic inflammation. Accordingly, the subject compounds and compositions can be useful in the treatment of chronic pain, migraines, thermal-induced pain, such as sunburn, or other thermal and nociceptive pain, and chronic pain associated with arthritis. Uses can also include other inflammatory conditions that involve a neurogenic pain-producing component, e.g, certain metastic carcinomas or inflammation of the blood vessels.

The compounds of the subject invention can be used to treat a variety of skin conditions including, but not limited to, radiation irritation and burns (including UV and ionizing), chemical burns, rhinitis, thermal burns, and reddening of the skin.

The compounds of the subject invention can also be used to treat allergic response and/or promote wound healing.

Following are examples which illustrate procedures, including the best mode, for practicing the invention. A more complete understanding of the invention can be obtained by reference to preferred embodiments of the invention, which are illustrated by the following specific examples of compounds, compositions, and methods of the invention. It will be apparent to those skilled in the art that the examples involve use of materials and reagents that are commercially available from known sources, e.g., chemical supply houses, so no details are given respecting them. These examples should not be construed as limiting. All percentages are by weight and all solvent mixture proportions are by volume unless otherwise noted.

EXAMPLE 1

Preparation of Topsentin, Bromotopsentin, and 4,5-dihydro-6"-deoxybromotopsentin Topsentin, bromotopsentin, and 4,5-dihydro-6"-deoxybromotopsentin can be obtained and prepared as described in U.S. Pat. No. 4,866,084, which is incorporated herein by reference.

EXAMPLE 2

Preparation of Homocarbonyl Topsentin and Homocarbonyl Topsentin Monoacetate

Homocarbonyl topsentin and homocarbonyl topsentin monoacetate can be obtained and prepared as described in U.S. Pat. Nos. 5,290,777 and 5,464,835, which are incorporated herein by reference.

EXAMPLE 3

Preparation of Topsentin Analogs and Derivatives

The conversion of bromotopsentin to topsentin; the preparation of 3-(hydroxyacetyl)indole, 3-chloroacetyl-6-(benzyloxy)indole, and 3-hydroxyacetyl-6-(benzyloxy) indole as synthons; the synthesis directly from (hydroxylacetyl)indoles of O-benzyltopsentin, O-benzylisotopsentin, O,O'-dibenzylhydroxytopsentin, and deoxytopsentin I(e); the preparation of compounds I(e) and O-benzyltopsentin, O-benzylisotopsentin, and O,O'-dibenzylhydroxytopsentin from isolated glyoxal intermediates; the conversion of O-benzyltopsentin to topsentin I(a); the conversion of O-benzylisotopsentin to isotopsentin I(c); the synthesis of hydroxytopsentin I(d) from 3-hydroxyacetyl-6-(benzyloxy)-indole; preparation of 3-chloroacetyl-5-benzyl(oxy)indole; the preparation of 3-hydroxyacetyl-5-(benzyloxy)indole; synthesis of neohydroxytopsentin I(h); and synthesis of neotopsentin I(f) and neoisotopsentin I(g) are described in U.S. Pat. No. 4,866,084, which has been incorporated herein by reference. Topsentin monoacetate III(k), topsentin diacetate III(I), and bromotopsentin-O-mesylate I(i) can also be converted from topsentin or its analogs by methods well known and readily available to those skilled in the art.

NMR data of bromotopsentin-O-mesylate:

$^1$H NMR (500 MHz, DMSO-$d_6$) δ 3.384 (3 H, s), 7.242 (1 H, dd, J=7.0, 1.5 Hz), 7.544 (1 H, d, J=2.0 Hz), 7.638 (1 H, d, J=1.0 Hz), 7.729 (1 H, s), 7.997 (1 H, s), 8.421 (1 H, d, J=9.0 Hz), 9.281 (1 H, s), 11.511 (1 H, s), 12.272 (1 H, s).

EXAMPLE 4

Isolation of Nortopsentin A, B, & C

Nortopsentin compounds can be obtained and prepared as described in U.S. Pat. No. 4,970,226, which is incorporated herein by reference.

EXAMPLE 5

Preparation of Dragmacidin (VI)

Dragmacidin compounds can be obtained and prepared as described in U.S. Pat. No. 4,895,844, which is incorporated herein by reference. The '844 patent refers to Dragmacidin (VI) as "biemnidin."

EXAMPLE 6

Preparation of Hamacanthins

Hamacanthin compounds can be obtained and prepared as described in U.S. Pat. No. 5,464,835, which is incorporated herein by reference.

EXAMPLE 7

Preparation of Dragmacidin d (IX)

Taxonomic and collection data. A sample of Spongosorites n. sp. (HBOM catalog number 003:00544) was collected by the Johnson Sea Link manned submersible at a depth of 292 feet at York Bay, St. Vincent, Grenadines. This new species is a massive amorphous thickly encrusting sponge, dark yellow alive and dark brown in ethanol preservative. Vermetid gastropods are associated wth and incorporated into the sponge. The consistency is firm but crumbly. The genus is characterized by a distinct dermal layer of smaller spicules arranged tangentially to the surface of the sponge and a confused choanasomal arrangement of spicules with sporadic spicule tracks (30–100 µm in width) running parallel to the surface. In 003:00544, there are two categories of oxeas, some of which are slightly flexed at the midpoint. This new species is most similar to *S. ruetzleri* from which it is distinguished by the absence of bromotopsentin.

Isolation of dragmacidin d (IX). 100 g of the frozen sponge was extracted exhaustively with ethanol by macerating in a Waring blender. The extract was filtered through a bed of Celite and then concentrated to a red-orange oil by distillation under reduced pressure. The residue was chromatographed under vacuum column chromatogorahic conditions on an RP-18 stationary phase. The column was eluted with a step gradient of acetonitrile (ACN) in water containing 0.05% triflouroacetic acid (TFA). The column was eluted as follows; Fraction 1, 500 mL of water containing 0.05% TFA by volume; Fraction 2, 250 mL of water containing 0.05% TFA by volume; Fraction 3, 200 ml of water-ACN-TFA (160:40:0.1 v/v/v); fraction 4, 200 ml of water-ACN-TFA(120:80:0.1 v/v/v); fraction 5, 200 ml of water-ACN-TFA (80:120:0.1 v/v/v); fraction 6, 200 ml of water-ACN-TFA (40:160:0.1 v/v/v); fraction 7, 500 ml of ACN. Dragmacidin d eluted in Fractions 3, 4, and 5.

Spectral Data:

UV absorption: EtOH $\lambda_{max}$ 213(47,870), 270 sh, 278 (14470), 383 (20,740) after addition of one drop of HCl to a 2 mL cell: 214 (54,000), 280 (16,400), 452 (19,946).

IR absorption: (neat, microscope)$\upsilon_{max}$ (cm-1), 3165 broad, 1678, 1637, 1531, 1447, 1408, 1244, 1200, 1136, 955, 806.

$^1$H NMR (360 Mhz, d6-DMSO, trace of TFA): 11.88 (bs), 11.85 (bs), 11.75 (d, 2.7 Hz), 11.62 (d, 2.6 Hz), 8.80 (d, 2.7 Hz), 8.58 (d, 8.6 Hz), 7.69 (d, 1.7 Hz), 7.52 (d, 2.6 Hz), 7.50 (s), 7.34 (bs 2 H), 7.27 (dd, 8.6, 1.7 Hz), 6.61 (s), 6.61 (s), 6.37 (s), 4.33 (q, 6.8 Hz), 1.33 (d, 6.8 Hz, 3 H).

$^{13}$CNMR (90 Mhz, d6-DMSO, trace of TFA): 155.10 s, 148.46 s, 147.48, s, 143.10 s, 137.44 s, 131.51 d, 131.43 s, 131.16 s, 127.35 d, 126.94 s, 125.89 s, 125.59 s, 125.25 s, 124.60 d, 123.87 d, 123.32 d, 118.56 d, 115.11 s, 114.55 d, 113.55 d, 112.17 s, 108.98 d, 107.52 s, 106.54 d, 31.22 d, 20.48 q

EXAMPLE 8

Preparation of 2,2-bis(6-bromoindol-3-yl) ethyl amine (X)

Taxonomic and collection data. A sample of Spongosorites sp. (HBOM catalog number 003:00696) was collected by the Johnson Sea Link manned submersible at a depth of 927 feet at San Juan, Tenerife, Canary Islands. This specimen is massive and amorphous. It is white both internally and externally alive and light tan when frozen. Vermetid gastropods are associated with and incorporated into the sponge. The consistency is firm but crumbly.

Isolation of 2,2-bis(6-bromoindol-3-yl) ethyl amine (X). 20 g of the frozen sponge was extracted exhaustively with ethanol by macerating in a Waring blender. The extract was and then concentrated to 1.5 g of a brown oil by distillation under reduced pressure. 400 mg of the residue was chromatographed under vacuum column chromatogorahic conditions on an RP-18 stationary phase. The column (60 mL volume) was eluted with a step gradient of acetonitrile (ACN) in water containing 0.1% triflouroacetic acid (TFA). The column was eluted as follows; Fraction 1, 100 mL of water containing 0.1% TFA by volume; Fraction 2, 100 ml of water-ACN-TFA (80:20:0.1 v/v/v); fraction 3, 100 ml of water-ACN-TFA (60:40:0.1 v/v/v); fraction 4, 100 ml of water-ACN-TFA (40:60:0.1 v/v/v); fraction 5, 100 ml of water-ACN-TFA (20:80:0.1 v/v/v); fraction 6, 100 ml of ACN; fraction 7, 100 ml of methanol; fraction 8, 100 ml methanol:methylenechloride (1:1 v/v). 2,2-bis(6-bromoindol-3-yl) ethyl amine (X) eluted in Fractions 3, and 4 (69% of the extract by weight).

$^1$H NMR (500.3 MHz, d3-MeOD) 7.53 (2 H, d, J=1.6 Hz), 7.38 (2 H, d, J=8.8 Hz), 7.24 (2 H, s), 7.03 (2 H, dd J=8.8,1.6 Hz), 4.82 (1 H, m, J=7.5 Hz), 3.68 (2 H, d, J=7.5 Hz).

$^{13}$C NMR (125.7 MHz, d3-MeOD) 139.2 (s, 2H), 126.5 (s, 2 H), 124.7 (d, 2 H), 123.1 (d, 2 H), 121.0 (d, 2 H), 116.2 (s, 2 H), 115.4 (d, 2 H), 115.0 (s, 2 H), 44.4 (t), 34.1 (d).

EXAMPLE 9

Anti-Neurogenic Inflammatory Properties of Bis-Indole Compounds

The inhibition of inflammation activity of a particular compound can be demonstrated by a standard and accepted in vivo assay which employs capsaicin (CAP) to induce inflammation (edema) in an animal. The assay employing mice (e.g., administration to the ear of the mouse) is routinely used by those skilled in the art and is accepted as indicative of anti-inflammatory activity in humans. This assay is described below.

A. Inhibition of Capsaicin-Induced Inflammation (Edema) of the Mouse Ear. Induction of mouse ear edema was based on known methods. Inoue, H., Nagata, N., and Koshihara, Y. (1993). Profile of capsaicin-induced mouse ear oedema as neurogenic inflammatory model: comparison with arachidonic acid-induced ear oedema. *Br. J. Pharm* 110:161–20. Compounds to be tested for anti-neurogenic inflammatory activity are topically applied in acetone to the ears of mice in a solution that includes the edema-causing irritant, capsaicin (CAP). CAP alone (250 µg/ear) or in combination with various dilutions of test compound are applied to both sides of the left ears (5 mice per treatment group) and acetone is applied to all right ears. After a 30 minute incubation, the mice are sacrificed, the ears removed, and bores taken and weighed. Edema is measured by subtracting the weight of the right ear (acetone control) from the weight of the left ear (treated). Results are recorded as % decrease (inhibition) or % increase (potentiation) in edema relative to the control group edema.

Bis-heterocycle compounds of the subject invention, e.g., the bis-indole compounds, show significant anti-inflammatory properties. When screened for the ability to reduce edema in mouse ears caused by application of capsaicin (CAP), a known inflammatory agent, topsentin and bromotopsentin were found to have greater potency in inhibiting neurogenic inflammation than capsazepine, a synthetic analog of capsaicin and specific capsaicin antagonist. Capsazepine was screened as a positive control at 1500, 1000, and 500 µg/ear and inhibited CAP-induced edema by 76%, 52%, and 33%, respectively. Topsentin and bromotopsentin were screened at 500 µg/ear and inhibited CAP-induced inflammation by 74% and 79%, respectively. See Tables 1 and 2, below.

TABLE 1

Inhibition of capsaicin-induced mouse ear edema by capsazepine

| Treatment | Inflammation (mg) ± SEM | % Inhibition |
|---|---|---|
| Capsaicin Control 250 μg/ear | 6.6 ± 0.6 (n = 20) | — |
| Capsazepine 500 μg/ear | 4.4** ± 0.7 (n = 5) | 33 |
| Capsazepine 1000 μg/ear | 3.1* ± 1.0 (n = 5) | 52 |
| Capsazepine 1500 μg/ear | 1.6* ± 0.3 (n = 5) | 76 |

Statistically significant difference between control and treatment groups
Students t-test *(p < 0.01) **(p < 0.05)

TABLE 2

Inhibition of capsaicin-induced mouse ear edema by the topsentins

| Treatment | Inflammation (mg) ± SEM | % Inhibition |
|---|---|---|
| Capsaicin Control 250 μg/ear | 6.6 ± 0.6 (n = 20) | — |
| Topsentin 100 μg/ear | 4.8 ± 1.0 (n = 10) | 28 |
| Topsentin 250 μg/ear | 2.2* ± 0.2 (n = 10) | 66 |
| Topsentin 500 μg/ear | 1.7* ± 0.5 (n = 10) | 74 |
| Topsentin 1000 μg/ear | 0.7* ± 0.2 (n = 10) | 90 |
| Bromotopsentin 500 μg/ear | 1.4* ± 0.2 (n = 5) | 79 |

Statistically significant difference between control and treatment groups
*Students t-test (p < 0.01)

In consideration of the data presented, the subject bis-indole compounds have been shown to have potent anti-neurogenic inflammatory characteristics with unique clinical applications.

A dose-response curve for the inhibition of capsaicin-induced edema by topsentin was generated and is shown as FIG. 1. Specifically, the dose-response curve for topsentin, measured as percent inhibition of edema, shows topsentin having up to approximately 90% inhibition at a final concentration of about 1000 μM. In the mouse ear edema inhibition assay, a dose of about 100 μg/ear of topsentin achieved more than 25% inhibition of edema. The $ED_{50}$ of topsentin in inhibition of capsaicin-induced inflammation was about 200 μg/ear. Experiments using bromotopsentin were also conducted. Percent inhibition of mouse ear edema by 500 μg/ear of bromotopsentin resulted in about 79% inhibition, similar to the results shown for topsentin.

B. Inhibition of Resiniferatoxin (RTX)-induced edema in a mouse ear model. Topsentin was also tested for its inhibitory activity against inflammation induced by the neurogenic inflammation producing compound, resiniferatoxin (RTX). Using a mouse ear model, the experimental procedure is substantially the same as that described for the capsaicin-induced inflammation assay (see section A of this Example, above). Topsentin inhibited RTX-induced edema approximately 12% using an amount of as little as 5 μg topically applied to the ear. Use of about 100 μg on the ear inhibited RTX-induced edema nearly 100% in certain animals and averaged about 91%. These results are shown in more detail in Table 3, below.

Figure 2:
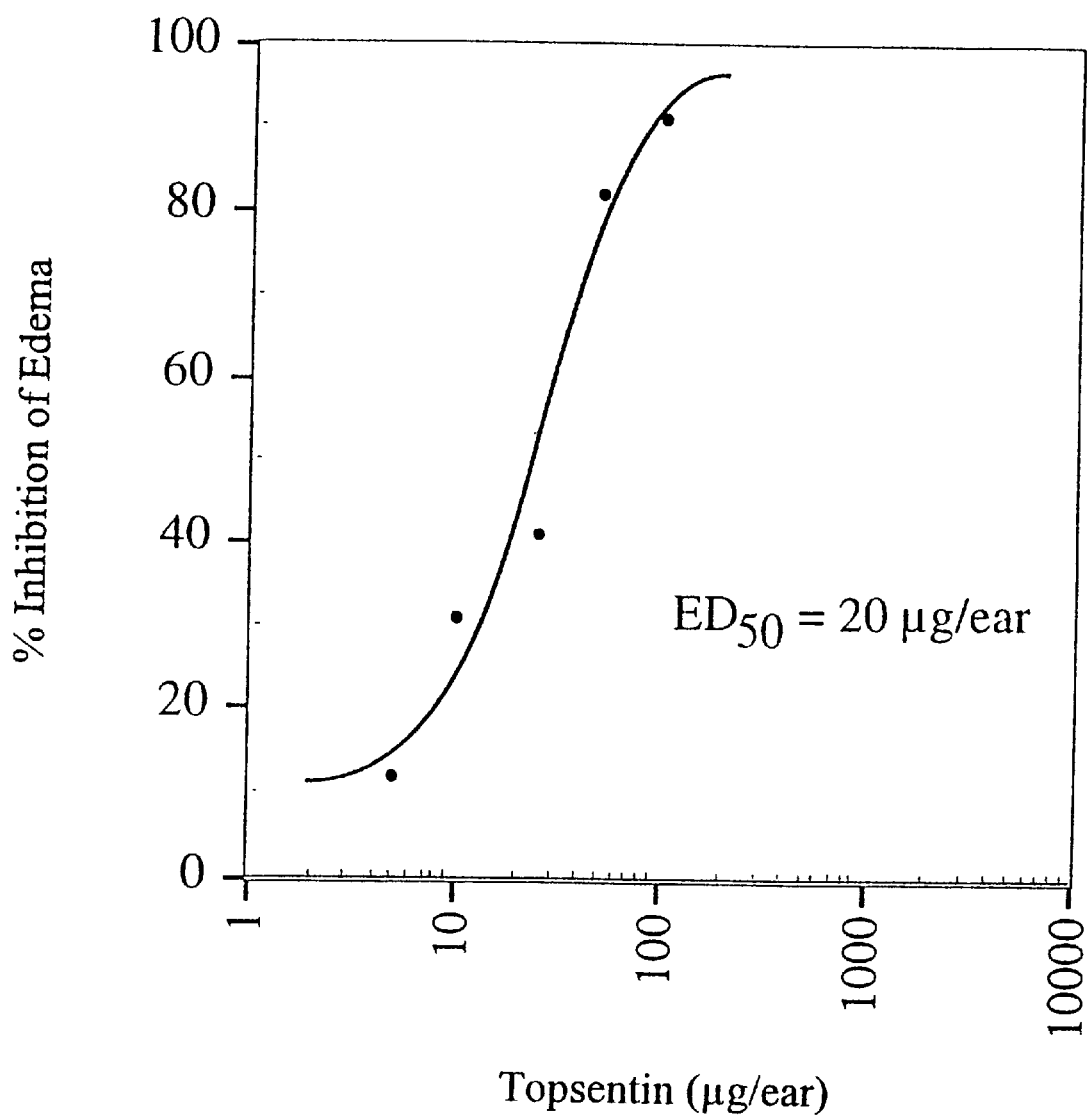
FIG. 2 shows a log dose response curve for a bis-heterocycle of the subject invention (topsentin) illustrating its inhibition of resiniferatoxin (RTX)-induced edema in a mouse ear model.

A dose-response curve for inhibition of RTX-induced edema by topsentin was generated, showing an ED50 of about 20 μg/ear. See FIG. 2.

TABLE 3

Inhibition of RTX-induced inflammation by topsentin

| Treatment | Right ear (mg) | Left ear (mg) | Difference (mg) | Mean | SEM | % Inh. of Edema |
|---|---|---|---|---|---|---|
| RTX control 0.1 μg/ear | | | n = 25 | 14.0 | 0.4 | — |
| Topsentin 100 μg/ear | 11.1 | 11.8 | 0.7 | 1.3 | 0.5 | 91 |
| | 12.1 | 13.3 | 1.2 | | | |
| | 11.8 | 12.4 | 0.6 | | | |
| | 11.3 | 12.6 | 1.3 | | | |
| | 11.6 | 11.8 | 0.2 | | | |
| | 11.8 | 13.1 | 1.3 | | | |
| | 11.6 | 16.9 | 5.3 | | | |
| | 11.4 | 13.0 | 1.6 | | | |
| | 11.3 | 11.6 | 0.3 | | | |
| | 10.8 | 10.8 | 0.0 | | | |
| Topsentin 50 μg/ear | 12.3 | 14.8 | 2.5 | 2.6 | 0.6 | 82 |
| | 12.8 | 18.8 | 6.0 | | | |
| | 12.2 | 16.3 | 4.1 | | | |
| | 11.8 | 12.1 | 0.3 | | | |
| | 11.6 | 13.6 | 2.0 | | | |
| | 11.8 | 15.9 | 4.1 | | | |
| | 11.2 | 12.6 | 1.4 | | | |
| | 11.7 | 15.9 | 4.2 | | | |
| | 11.3 | 12.4 | 1.1 | | | |
| | 10.9 | 11.0 | 0.1 | | | |
| Topsentin 25 μg/ear | 12.1 | 18.1 | 6.0 | 8.3 | 0.7 | 41 |
| | 11.7 | 19.4 | 7.7 | | | |
| | 10.7 | 20.2 | 9.5 | | | |
| | 12.0 | 22.5 | 10.5 | | | |
| | 11.2 | 16.6 | 5.4 | | | |

TABLE 3-continued

Inhibition of RTX-induced inflammation by topsentin

| Treatment | Right ear (mg) | Left ear (mg) | Difference (mg) | Mean | SEM | % Inh. of Edema |
|---|---|---|---|---|---|---|
|  | 11.4 | 19.4 | 8.0 |  |  |  |
|  | 11.8 | 22.8 | 11.0 |  |  |  |
|  | 11.2 | 18.0 | 6.8 |  |  |  |
|  | 11.4 | 18.4 | 7.0 |  |  |  |
|  | 11.6 | 22.9 | 11.3 |  |  |  |
| Topsentin | 10.5 | 17.8 | 7.3 | 9.6 | 1.1 | 31 |
| 10 μg/ear | 11.2 | 15.6 | 4.4 |  |  |  |
|  | 9.9 | 20.3 | 10.4 |  |  |  |
|  | 11.2 | 19.5 | 8.3 |  |  |  |
|  | 11.3 | 25.6 | 14.3 |  |  |  |
|  | 11.5 | 20.3 | 8.8 |  |  |  |
|  | 12 | 22.1 | 10.1 |  |  |  |
|  | 12.4 | 20.1 | 7.7 |  |  |  |
|  | 12.0 | 20.9 | 8.9 |  |  |  |
|  | 13.5 | 29.5 | 16.0 |  |  |  |
| Topsentin | 11.6 | 19.7 | 8.1 | 12.3 | 0.8 | 12 |
| 5 μg/ear | 11.9 | 24.8 | 12.9 |  |  |  |
|  | 12.1 | 22.4 | 10.3 |  |  |  |
|  | 11.3 | 22.3 | 11.0 |  |  |  |
|  | 11.4 | 25.6 | 14.2 |  |  |  |
|  | 11.5 | 23.5 | 12.0 |  |  |  |
|  | 11.6 | 22.8 | 11.2 |  |  |  |
|  | 11.0 | 28.0 | 17.0 |  |  |  |
|  | 11.2 | 22.7 | 11.5 |  |  |  |
|  | 12.6 | 26.9 | 14.3 |  |  |  |

Figure 3:
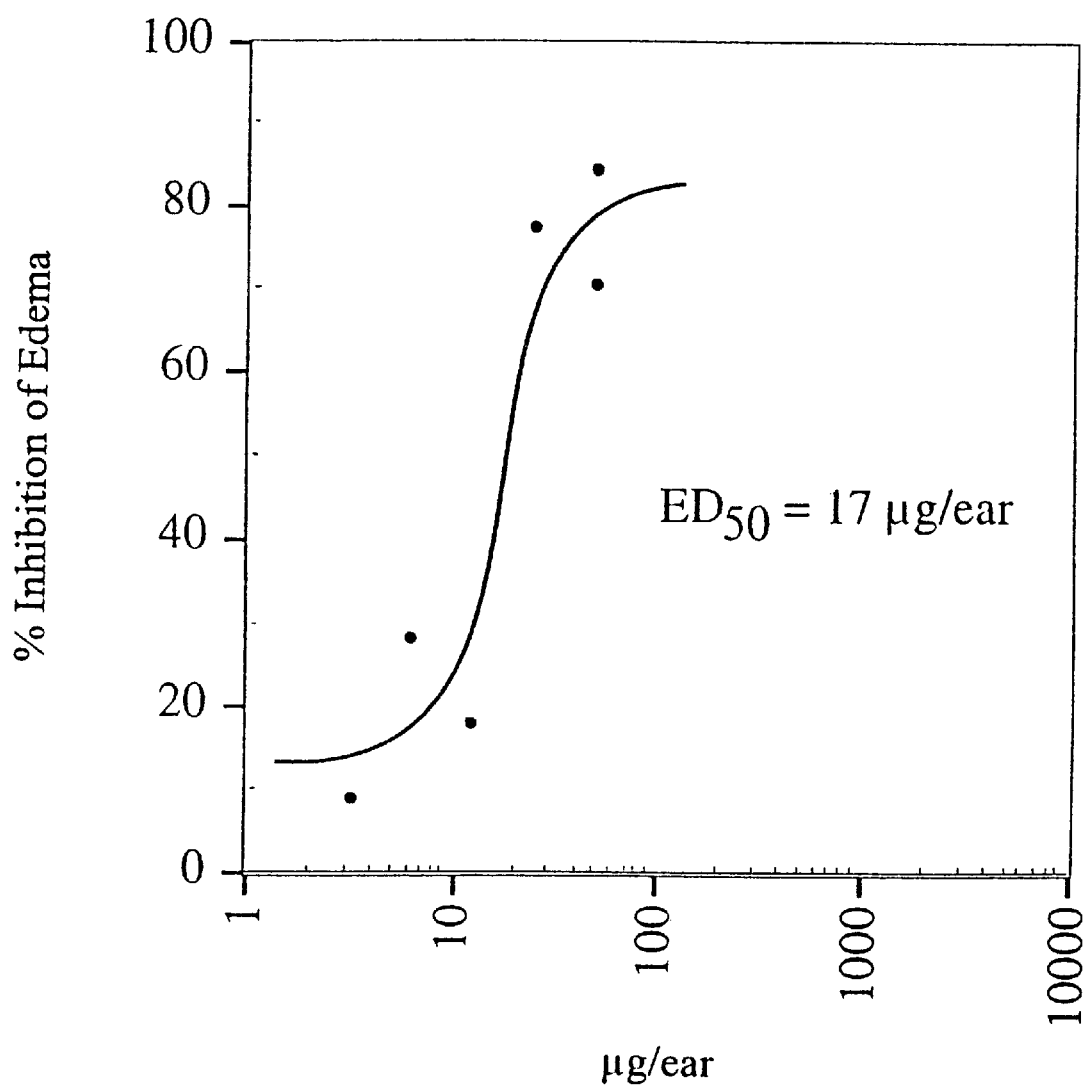
FIG. 3 shows a dose response curve for inhibition of RTX-induced edema by o-mesylbromotopsentin. $ED_{50}$ is about 17 µg/ear.

O-Mesylbromotopsentin HB227 was also tested for its inhibitory activity against inflammation induced by the neurogenic inflammation producing compound resiniferatoxin (RTX). o-Mesylbromotopsentin inhibited RTX-induced edema 28% using as little as 6.25 μg topically applied to the ear. Use of 50 μg on the ear inhibited 70% in certain animals. These results are shown in detail in Table 4 below. A dose response curve for inhibition of RTX-induced edema by o-Mesylbromotopsentin was generated, showing an $ED_{50}$ of about 17 μg/ear. See FIG. 3.

Figure 4:
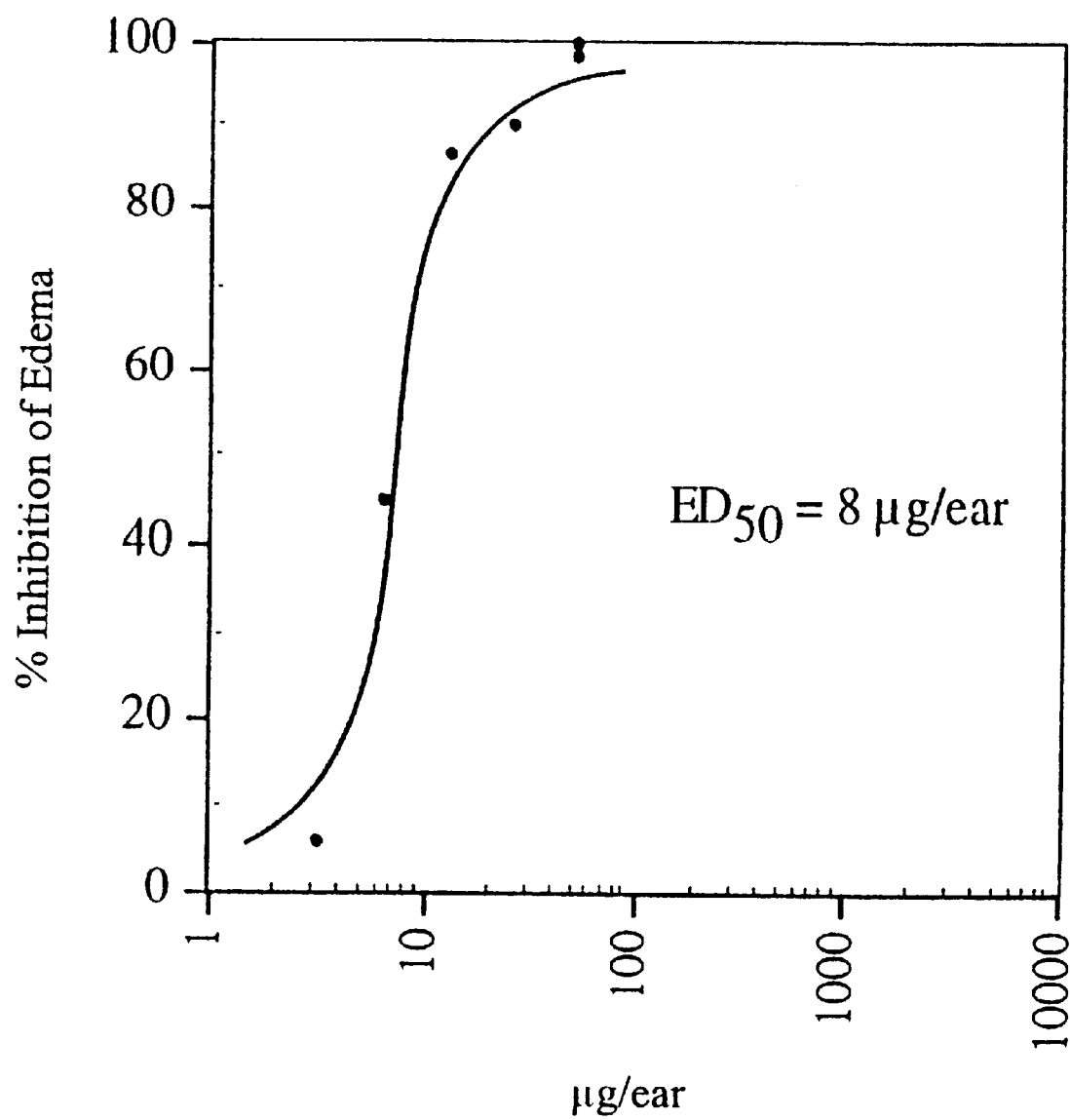
FIG. 4 shows a dose response curve for inhibition of RTX-induced edema by nortopsentin c. $ED_{50}$ is about 8 µg/ear.

Nortopsentin c was also tested for its inhibitory activity against inflammation induced by the neurogenic inflammation producing compound resiniferatoxin (RTX). Nortopsentin c inhibited RTX-induced edema 45% using as little as 6.25 μg topically applied to the ear. Use of 50 μg on the ear inhibited nearly 100% in certain animals and averaged about 98%. These results are shown in detail in Table 5 below. A dose response curve for inhibition of RTX-induced edema by Nortopsentin c was generated, showing an $ED_{50}$ of about 8 μg/ear. See FIG. 4.

Figure 5:
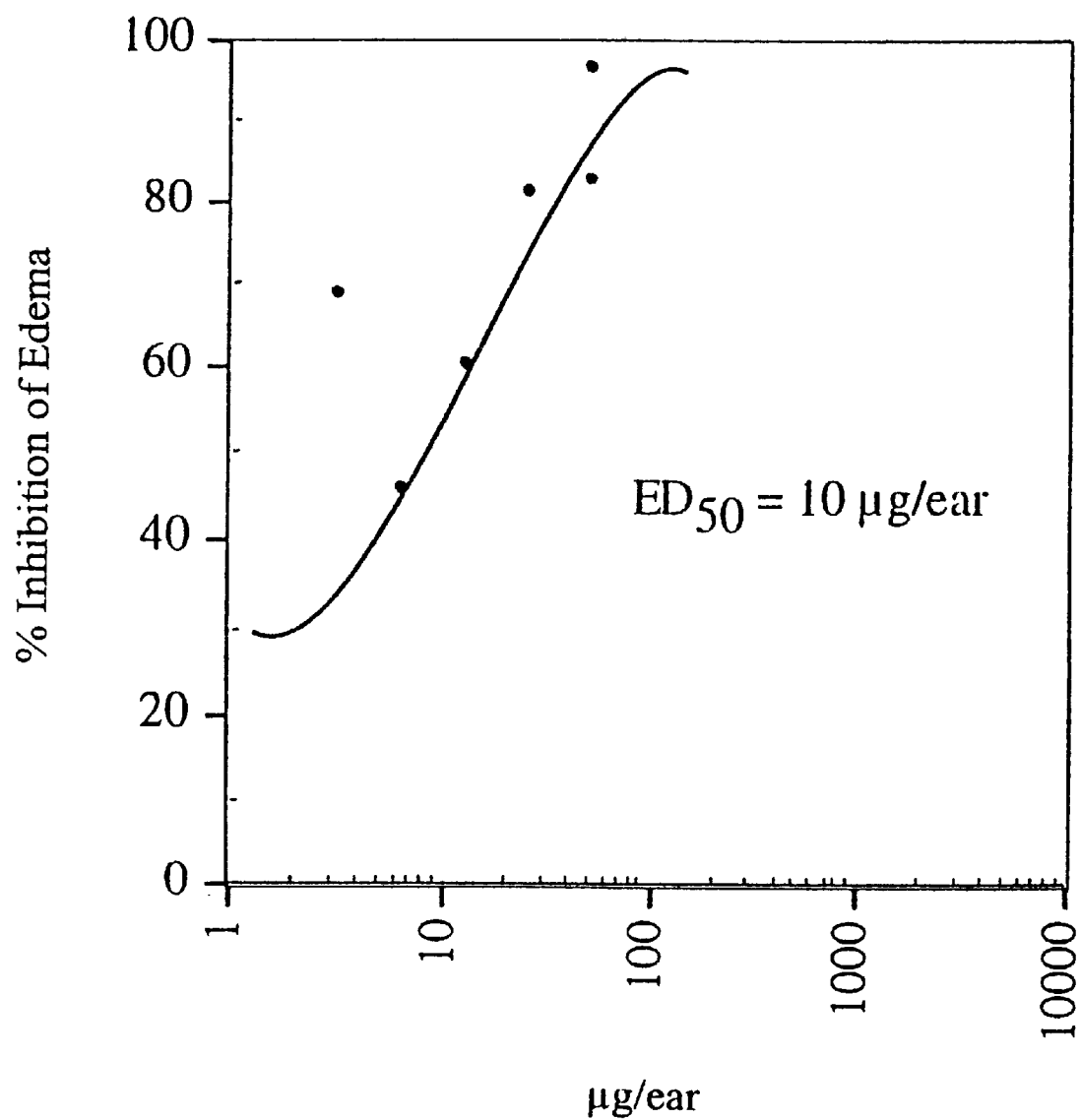
FIG. 5 shows a dose response curve for inhibition of RTX-induced edema by hamacanthin b. $ED_{50}$ is about 1.5 µg/ear.

Hamacanthin b was also tested for its inhibitory activity against inflammation induced by the neurogenic inflammation producing compound resiniferatoxin (RTX). Hamacanthin b inhibited RTX-induced edema 68% using as little as 3.12 μg topically applied to the ear. Use of 50 μg on the ear inhibited nearly 100% in certain animals and averaged about 97%. These results are shown in detail in Table 6 below. A dose response curve for inhibition of RTX-induced edema by Hamacanthin b was generated, showing an $ED_{50}$ of about 1.5 μg/ear. See FIG. 5.

Figure 6:
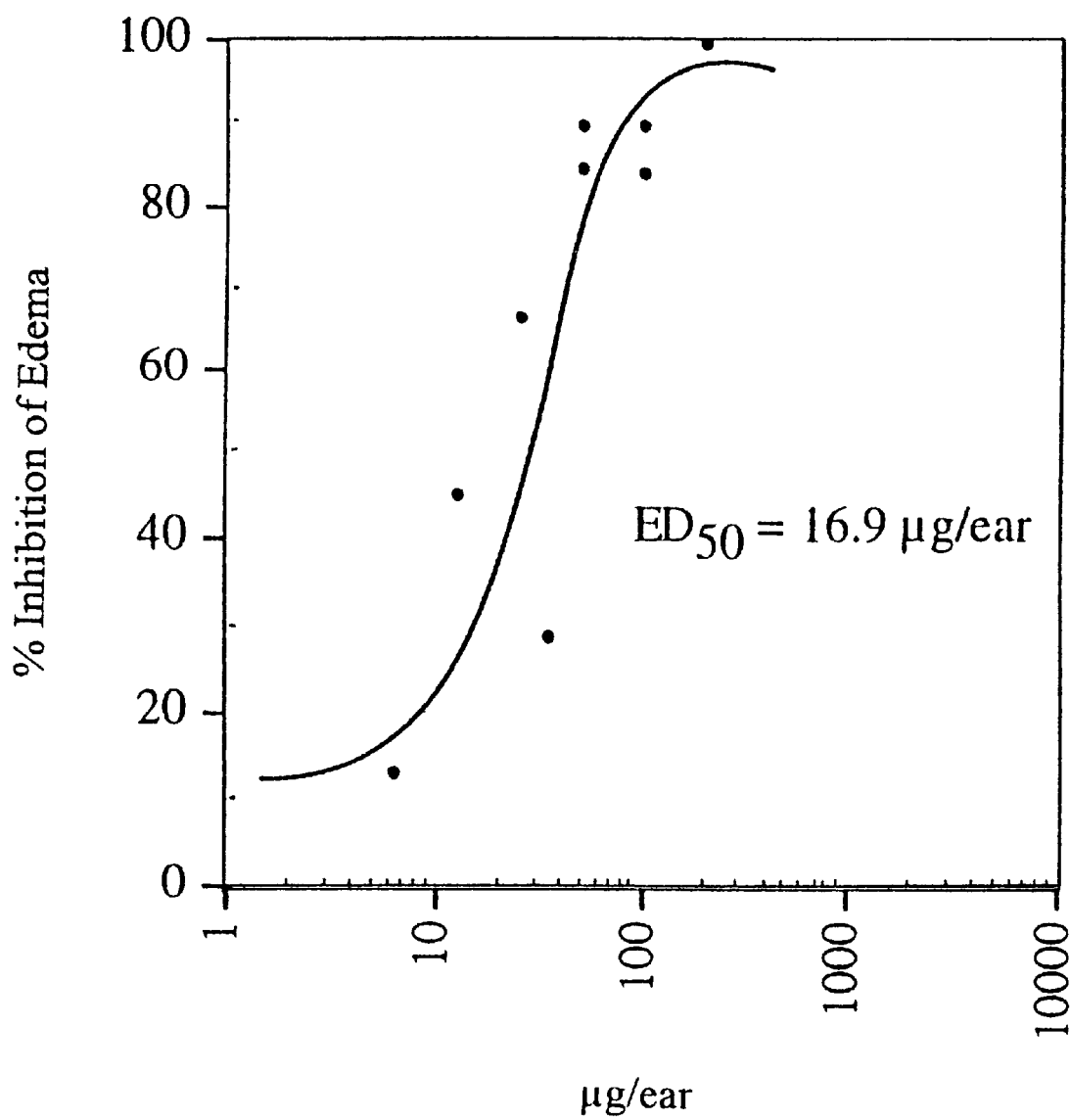
FIG. 6 shows a dose response curve for inhibition of RTX-induced edema by deoxytopsentin. $ED_{50}$ is about 17 µg/ear.

Deoxytopsentin was also tested for its inhibitory activity against inflammation induced by the neurogenic inflammation producing compound resiniferatoxin (RTX). Deoxytopsentin inhibited RTX-induced edema 13% using as little as 6.25 μg topically applied to the ear. Use of 100 μg on the ear inhibited nearly 100% in certain animals and averaged about 90%. These results are shown in detail in Table 7 below. A dose response curve for inhibition of RTX-induced edema by Deoxytopsentin was generated, showing an $ED_{50}$ of about 17 μg/ear. See FIG. 6.

Figure 7:
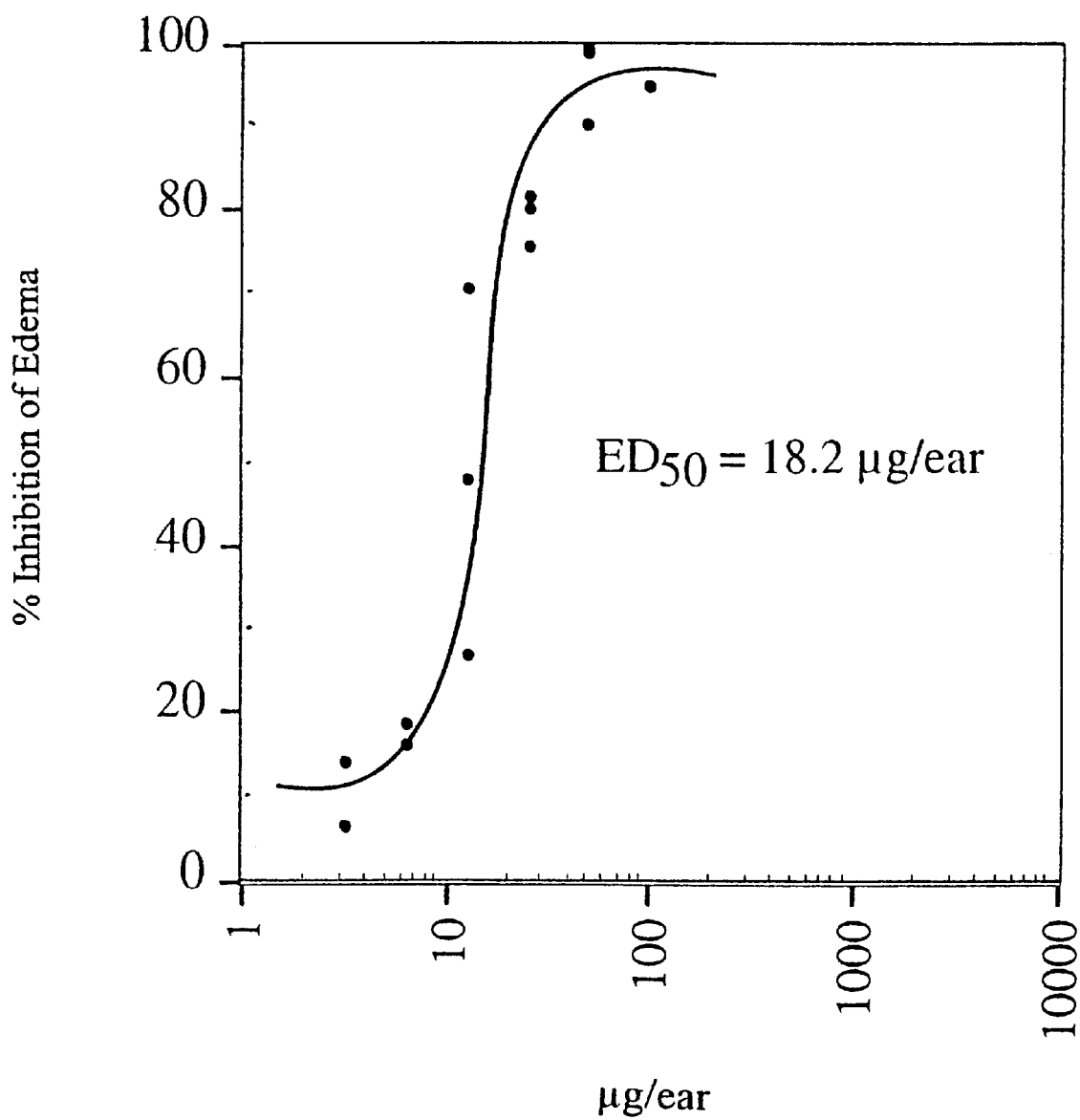
FIG. 7 shows a dose response curve for inhibition of RTX-induced edema by 2,2-bis(6-bromoindol-3-yl) ethyl amine. $ED_{50}$ is about 18.1 µg/ear.

2,2-bis(6-bromoindol-3-yl) ethyl amine was also tested for its inhibitory activity against inflammation induced by the neurogenic inflammation producing compound resiniferatoxin (RTX). 2,2-bis(6-bromoindol-3-yl) ethyl amine inhibited RTX-induced edema 18% using as little as 6.25 μg topically applied to the ear. Use of 50 μg on the ear inhibited nearly 100% in certain animals and averaged about 99%. These results are shown in detail in Table 8 below. A dose response curve for inhibition of RTX-induced edema by 2,2-bis(6-bromoindol-3-yl) ethyl amine was generated, showing an $ED_{50}$ of about 18.1 μg/ear. See FIG. 7.

TABLE 4

Inhibition of RTX-induced inflammation by O-mesylbromotopsentin

| Treatment | Right ear (mg) | Left ear (mg) | Difference (mg) | Mean | St. Dev. | SEM | % Inh. of Edema |
|---|---|---|---|---|---|---|---|
| RTX Control | 10.8 | 26.2 | 15.4 | 10.1 | 4.1 | 1.8 |  |
| 0.1 μg/ear | 9.2 | 17.6 | 8.4 |  |  |  |  |
|  | 9.7 | 17.8 | 8.1 |  |  |  |  |
|  | 10.5 | 23.9 | 13.4 |  |  |  |  |

TABLE 4-continued

Inhibition of RTX-induced inflammation by O-mesylbromotopsentin

| Treatment | Right ear (mg) | Left ear (mg) | Difference (mg) | Mean | St. Dev. | SEM | % Inh. of Edema |
|---|---|---|---|---|---|---|---|
| | 9.6 | 22.8 | 13.2 | | | | |
| o-mesylbromotopsentin | 9.0 | 13.2 | 4.2 | 3 | 1.4 | 0.6 | 70.3 |
| 50 µg/ear | 9.5 | 10.2 | 0.7 | | | | |
| | 10.7 | 13.5 | 2.8 | | | | |
| | 11.1 | 15.3 | 4.2 | | | | |
| | 11.6 | 14.7 | 3.1 | | | | |
| o-mesylbromotopsentin | 9.7 | 11.0 | 1.3 | 2.3 | 1.6 | 0.7 | 77.6 |
| 25 µg/ear | 10.6 | 11.9 | 1.3 | | | | |
| | 11.7 | 12.5 | 0.8 | | | | |
| | 9.9 | 14.0 | 4.1 | | | | |
| | 11.3 | 15.1 | 3.8 | | | | |
| o-mesylbromotopsentin | 11.2 | 16.6 | 5.4 | 8.3 | 2.1 | 0.9 | 86.8 |
| 12.5 µg/ear | 10.9 | 17.8 | 6.9 | | | | |
| | 9.6 | 19.1 | 9.5 | | | | |
| | 9.3 | 18.5 | 9.2 | | | | |
| | 10.6 | 21.0 | 10.4 | | | | |
| o-mesylbromotopsentin | 10.6 | 17.0 | 6.4 | 7.2 | 1.1 | 0.5 | 28.3 |
| 6.25 µg/ear | 9.1 | 18.0 | 8.9 | | | | |
| | 10.0 | 17.4 | 7.4 | | | | |
| | 10.5 | 18.2 | 7.7 | | | | |
| | 10.4 | 17.4 | 7.0 | | | | |
| o-mesylbromotopsentin | 9.1 | 22.0 | 12.9 | 9.2 | 3.1 | 1.4 | 8.9 |
| 3.12 µg/ear | 8.9 | 14.8 | 5.9 | | | | |
| | 10.1 | 16.2 | 6.1 | | | | |
| | 10.4 | 21.6 | 11.2 | | | | |
| | 10 | 19.9 | 9.9 | | | | |

TABLE 5

Inhibition of RTX-induced inflammation by nortopsentin c

| Treatment | Right ear (mg) | Left ear (mg) | Difference (mg) | Mean | St. Dev. | SEM | % Inh. of Edema |
|---|---|---|---|---|---|---|---|
| RTX Control | 11.1 | 20.3 | 9.2 | 9.8 | 2.4 | 1.1 | |
| 0.1 µg/ear | 10.3 | 20.0 | 9.7 | | | | |
| | 10.2 | 17.3 | 7.1 | | | | |
| | 11.1 | 23.9 | 12.8 | | | | |
| | 10.9 | 20.5 | 9.6 | | | | |
| nortopsentin c | 10.3 | 10.3 | 0.0 | 0.2 | 0.5 | 0.2 | 98.4 |
| 50 µg/ear | 11.3 | 11.0 | −0.3 | | | | |
| | 10.7 | 11.6 | 0.9 | | | | |
| | 11.0 | 10.7 | −0.3 | | | | |
| | 11.3 | 11.8 | 0.5 | | | | |
| nortopsentin c | 10.7 | 11.0 | 0.3 | 1.0 | 0.6 | 0.3 | 90.2 |
| 25 µg/ear | 10.6 | 11.8 | 1.2 | | | | |
| | 10.1 | 11.7 | 1.6 | | | | |
| | 10.0 | 11.3 | 1.3 | | | | |
| | 11.5 | 11.9 | 0.4 | | | | |
| nortopsentin c | 10.4 | 11.9 | 1.5 | 1.3 | 1.1 | 0.5 | 86.8 |
| 12.5 µg/ear | 13.0 | 13.0 | 0.0 | | | | |
| | 13.0 | 15.1 | 2.1 | | | | |
| | 10.9 | 13.4 | 2.5 | | | | |
| | 11.4 | 11.8 | 0.4 | | | | |
| nortopsentin c | 10.7 | 13.9 | 3.2 | 5.4 | 1.7 | 0.8 | 45.1 |
| 6.25 µg/ear | 11.0 | 18.7 | 7.7 | | | | |
| | 11.6 | 17.4 | 5.8 | | | | |
| | 11.1 | 15.4 | 4.3 | | | | |
| | 11.6 | 17.6 | 6.0 | | | | |
| nortopsentin c | 11.6 | 25.6 | 14.0 | 9.3 | 3.0 | 1.4 | 5.9 |
| 3.12 µg/ear | 10.3 | 17.7 | 7.4 | | | | |
| | 10.2 | 18.0 | 7.8 | | | | |
| | 11.1 | 21.6 | 10.5 | | | | |
| | 12.0 | 18.6 | 6.6 | | | | |

TABLE 6

Inhibition of RTX-induced inflammation by hamacanthin b

| Treatment | Right ear (mg) | Left ear (mg) | Difference (mg) | Mean | St. Dev. | SEM | % Inh. of Edema |
|---|---|---|---|---|---|---|---|
| RTX Control 0.1 µg/ear | 10.6 | 21.5 | 10.9 | 12.4 | 1.8 | 0.8 | |
| | 10.4 | 24.4 | 14.0 | | | | |
| | 10.0 | 24.0 | 14.0 | | | | |
| | 11.0 | 23.9 | 12.9 | | | | |
| | 11.0 | 23.9 | 12.9 | | | | |
| hamacanthin b 50 µg/ear | 10.6 | 10.8 | 0.2 | 0.4 | 0.6 | 0.3 | 96.9 |
| | 10.2 | 10.4 | 0.2 | | | | |
| | 11.6 | 11.6 | 0.0 | | | | |
| | 9.4 | 10.8 | 1.4 | | | | |
| | 9.5 | 9.6 | 0.1 | | | | |
| hamacanthin b 25 µg/ear | 10.7 | 13.0 | 2.3 | 2.3 | 1.2 | 0.5 | 81.6 |
| | 10.2 | 14.4 | 4.2 | | | | |
| | 9.2 | 11.2 | 2.0 | | | | |
| | 10.2 | 11.2 | 1.0 | | | | |
| | 10.6 | 12.5 | 1.9 | | | | |
| hamacanthin b 12.5 µg/ear | 11.1 | 15.7 | 4.6 | 4.9 | 2.5 | 1.1 | 86.8 |
| | 9.6 | 13.7 | 4.1 | | | | |
| | 10.5 | 16.6 | 6.1 | | | | |
| | 10.0 | 18.3 | 8.3 | | | | |
| | 10.1 | 11.5 | 1.4 | | | | |
| hamacanthin b 6.25 µg/ear | 10.3 | 17.2 | 6.9 | 6.7 | 1.3 | 0.6 | 46.0 |
| | 10.8 | 18.2 | 7.4 | | | | |
| | 10.4 | 17.4 | 7.0 | | | | |
| | 10.1 | 18.5 | 8.4 | | | | |
| | 9.9 | 15.3 | 5.4 | | | | |
| hamacanthin b 3.12 µg/ear | 9.0 | 13.4 | 4.4 | 3.9 | 2.5 | 1.1 | 68.8 |
| | 10.2 | 17.1 | 6.9 | | | | |
| | 11.1 | 12.6 | 1.5 | | | | |
| | 10.3 | 11.5 | 1.2 | | | | |
| | 10.9 | 16.2 | 5.3 | | | | |

TABLE 7

Inhibition of RTX-induced inflammation by deoxytopsentin

| Treatment | Right ear (mg) | Left ear (mg) | Difference (mg) | Mean | St. Dev. | SEM | % Inh. of Edema |
|---|---|---|---|---|---|---|---|
| RTX Control 0.1 ug/ml | 11.5 | 28.8 | 17.3 | 10.9 | 2.7 | 0.9 | |
| | 12.4 | 20.5 | 8.1 | | | | |
| | 11.4 | 20.6 | 9.2 | | | | |
| | 11.0 | 23.9 | 12.9 | | | | |
| | 11.9 | 21.3 | 9.4 | | | | |
| | 12.2 | 21.7 | 9.5 | | | | |
| | 11.3 | 22.8 | 11.5 | | | | |
| | 11.1 | 24.5 | 13.4 | | | | |
| | 9.6 | 20.3 | 10.7 | | | | |
| | 10.7 | 19.8 | 9.1 | | | | |
| Deoxytopsentin 100 ug/ml | 10.9 | 11.8 | 0.9 | 1.1 | 1 | 0.3 | 89.7 |
| | 10.4 | 10.8 | 0.4 | | | | |
| | 10.6 | 13.1 | 2.5 | | | | |
| | 10.6 | 13.7 | 3.1 | | | | |
| | 9.7 | 11.4 | 1.7 | | | | |
| | 12.0 | 12.4 | 0.4 | | | | |
| | 9.8 | 10.2 | 0.4 | | | | |
| | 11.5 | 12.9 | 1.4 | | | | |
| | 11.3 | 11.7 | 0.4 | | | | |
| | 11.1 | 11.1 | 0.0 | | | | |
| Deoxytopsentin 50 ug/ml | 9.6 | 11.8 | 2.2 | 1.7 | 0.9 | 0.3 | 84.4 |
| | 10.8 | 12.1 | 1.3 | | | | |
| | 11.5 | 17.4 | 5.9 | | | | |
| | 9.4 | 11.9 | 2.5 | | | | |
| | 9.4 | 11.6 | 2.2 | | | | |
| | 10.2 | 12.5 | 2.3 | | | | |
| | 12.5 | 15.6 | 3.1 | | | | |
| | 11.8 | 12.5 | 0.7 | | | | |
| | 10.8 | 12.3 | 1.5 | | | | |
| | 10.3 | 10.8 | 0.5 | | | | |
| Deoxytopsentin 25 ug/ml | 9.4 | 11.7 | 2.3 | 3.7 | 2.5 | 0.8 | 66.5 |
| | 10.3 | 13.1 | 2.8 | | | | |
| | 9.4 | 19.3 | 9.9 | | | | |

TABLE 7-continued

Inhibition of RTX-induced inflammation by deoxytopsentin

| Treatment | Right ear (mg) | Left ear (mg) | Difference (mg) | Mean | St. Dev. | SEM | % Inh. of Edema |
|---|---|---|---|---|---|---|---|
| | 10.3 | 12.9 | 2.6 | | | | |
| | 10.3 | 13.3 | 3.0 | | | | |
| | 10.4 | 11.3 | 0.9 | | | | |
| | 10.3 | 12.4 | 2.1 | | | | |
| | 11.2 | 15.6 | 4.4 | | | | |
| | 9.3 | 13.7 | 4.4 | | | | |
| | 11.3 | 15.4 | 4.1 | | | | |
| Deoxytopsentin 12.5 ug/ml | 10.2 | 17.4 | 7.2 | 6 | 2.8 | 0.9 | 45.1 |
| | 10.9 | 14.9 | 4.0 | | | | |
| | 10.7 | 23.1 | 12.4 | | | | |
| | 11.9 | 16.0 | 4.1 | | | | |
| | 13.5 | 19.1 | 5.6 | | | | |
| | 10.7 | 16.2 | 5.5 | | | | |
| | 12.0 | 19.2 | 7.2 | | | | |
| | 11.5 | 15.7 | 4.2 | | | | |
| | 11.0 | 18.0 | 7.0 | | | | |
| | 12.4 | 14.9 | 2.5 | | | | |
| Deoxytopsentin 6.25 ug/ml | 9.7 | 20.5 | 10.8 | 9.5 | 1.7 | 0.6 | 13.1 |
| | 11.6 | 18.3 | 6.7 | | | | |
| | 11.9 | 21.6 | 9.7 | | | | |
| | 12.6 | 21.5 | 8.9 | | | | |
| | 12.7 | 22.0 | 9.3 | | | | |
| | 11.6 | 22.0 | 10.4 | | | | |
| | 11.0 | 20.7 | 9.7 | | | | |
| | 11.5 | 17.9 | 6.4 | | | | |
| | 13.0 | 23.8 | 10.8 | | | | |
| | 11.1 | 22.9 | 11.8 | | | | |

TABLE 8

Inhibition of RTX-induced inflammation by 2,2-bis(6-bromoindol-3-yl)ethylamine

| Treatment | Right ear (mg) | Left ear (mg) | Difference (mg) | Mean | St. Dev. | SEM | % Inh. of Edema |
|---|---|---|---|---|---|---|---|
| RTX Control 0.1 µg/ear | 10.4 | 24.4 | 14.0 | 11.1 | 2.5 | 1.1 | |
| | 10.1 | 17.8 | 7.7 | | | | |
| | 10.6 | 21.5 | 10.9 | | | | |
| | 11.0 | 23.9 | 12.9 | | | | |
| | 11.0 | 21.1 | 10.1 | | | | |
| 2,2-bis(6-bromoindol-3yl)ethylamine 50 µg/ear | 12.5 | 11.8 | −0.7 | 0.1 | 0.9 | 0.4 | 99.3 |
| | 10.2 | 11.0 | 0.8 | | | | |
| | 10.4 | 11.6 | 1.2 | | | | |
| | 11.9 | 11.4 | −0.5 | | | | |
| | 10.8 | 10.4 | −0.4 | | | | |
| 2,2-bis(6-bromoindol-3yl)ethylamine 25 µg/ear | 11.1 | 14.5 | 3.4 | 2.1 | 1.1 | 0.5 | 81.5 |
| | 10.5 | 12.4 | 1.9 | | | | |
| | 11.6 | 12.7 | 1.1 | | | | |
| | 10.5 | 13.4 | 2.9 | | | | |
| | 10.7 | 11.7 | 1.0 | | | | |
| 2,2-bis(6-bromoindol-3yl)ethylamine 12.5 µg/ear | 10.0 | 16.5 | 6.5 | 5.8 | 3.2 | 1.4 | 86.8 |
| | 10.0 | 17.6 | 7.6 | | | | |
| | 10.6 | 20.5 | 9.9 | | | | |
| | 10.1 | 12.8 | 2.7 | | | | |
| | 9.6 | 12.0 | 2.4 | | | | |
| 2,2-bis(6-bromoindol-3yl)ethylamine 6.25 µg/ear | 10.7 | 28.5 | 17.8 | 13.2 | 3.4 | 1.5 | 18.5 |
| | 11.2 | 20.2 | 9.0 | | | | |
| | 10.3 | 17.4 | 7.1 | | | | |
| | 10.8 | 23.3 | 12.5 | | | | |
| | 10.9 | 22.2 | 11.3 | | | | |
| 2,2-bis(6-bromoindol-3yl)ethylamine 3.12 µg/ear | 10.0 | 22.8 | 12.8 | 11.9 | 5.6 | 2.5 | 6.8 |
| | 9.3 | 28.1 | 18.8 | | | | |
| | 9.9 | 17.9 | 8.0 | | | | |
| | 10.4 | 15.2 | 4.8 | | | | |
| | 10.8 | 25.8 | 15.0 | | | | |

TABLE 9

Inhibition of RTX-induced inflammation by Dragmacidin d

| Treatment | Right ear (mg) | Left ear (mg) | Difference (mg) | Mean | St. Dev. | SEM | % Inh. of Edema |
|---|---|---|---|---|---|---|---|
| RTX Control | 10.3 | 26.8 | 16.5 | 13.3 | 3.1 | 1.4 | |
| 0.1 µg/ear | 9.2 | 22.6 | 13.4 | | | | |
| | 10.1 | 20.3 | 10.2 | | | | |
| | 9.5 | 25.6 | 16.1 | | | | |
| | 10.5 | 20.7 | 10.2 | | | | |
| Dragmacidin d | 9.4 | 11.8 | 2.47 | 1.4 | 1.6 | 0.7 | 89.6 |
| 50 µg/ear | 11.3 | 10.9 | −0.4 | | | | |
| | 10.1 | 13.0 | 2.9 | | | | |
| | 9.9 | 12.3 | 2.4 | | | | |
| | 10.5 | 10.1 | −0.4 | | | | |

TABLE 10

Inhibition of RTX-induced inflammation by 4,5-dihydro-6"-deoxybromotopsentin

| Treatment | Right ear (mg) | Left ear (mg) | Difference (mg) | Mean | St. Dev. | SEM | % Inh. of Edema |
|---|---|---|---|---|---|---|---|
| RTX Control | 9.0 | 18 | 9.0 | 10.0 | 1.2 | 0.6 | |
| 0.1 µg/ear | 10.1 | 19.4 | 8.3 | | | | |
| | 8.9 | 18 | 9.1 | | | | |
| | 9.5 | 20.6 | 11.1 | | | | |
| | 8.5 | 20.1 | 11.6 | | | | |
| 4,5-dihydro-6"- | 9.7 | 13.5 | 3.8 | 3.3 | 2.1 | 0.9 | 87.1 |
| deoxybromotopsentin | 9.8 | 18.0 | 6.2 | | | | |
| 50 µg/ear | 9.0 | 12.8 | 3.8 | | | | |
| | 10.8 | 12.8 | 2.2 | | | | |
| | 11.0 | 11.5 | 0.5 | | | | |
| Nortopsentin A | 10.3 | 9.9 | −0.4 | −0.4 | 0.7 | 0.3 | 100 |
| 50 µg/ear | 10.1 | 10.8 | 0.7 | | | | |
| *pink | 9.4 | 9.0 | −0.4 | | | | |
| | 9.0 | 8.3 | −0.7 | | | | |
| | 10.1 | 8.8 | −1.3 | | | | |
| Nortopsentin B | 7.6 | 9.1 | 1.5 | 0.9 | 0.7 | 0.3 | 91.2 |
| 50 µg/ear | 9.3 | 9.5 | 0.2 | | | | |
| *pink | 8.8 | 9.9 | 1.1 | | | | |
| | 8.9 | 9.0 | 0.1 | | | | |
| | 8.5 | 10.0 | 1.5 | | | | |

EXAMPLE 10

Formulation and Administration

The compounds of the invention are useful for various non-therapeutic and therapeutic purposes. It is apparent from the testing that the compounds of the invention are effective for anti-inflammatory uses.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

In a preferred embodiment, the compounds or compositions of the subject invention are administered in a lotion or other cosmetic preparation. This administration is done directly to the skin where anti-inflammatory activity is desired.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the bis-heterocycle compounds, e.g., a bis-indole, as a first active ingredient plus a second active ingredient comprising an anti-inflammatory compound known in the art. Such known anti-inflammatory drugs include, but are not limited to, the steroidal anti-inflammatory drugs and the non-steroidal anti-inflammatory drugs (NSAIDs).

In accordance with this invention, pharmaceutically effective amounts of a known anti-inflammatory agent and the bis-heterocycle compounds are administered sequentially or concurrently to the patient. The most effective mode of administration and dosage regimen of bis-heterocycle compounds and anti-inflammatory agent will depend upon the type of condition to be treated, the severity and course of that condition, previous therapy, the patient's health status, and response to bis-indoles and the judgment of the treating physician. Bis-heterocycle compositions may be administered to the patient at one time or over a series of treatments.

Preferably, the bis-heterocycle, e.g., a bis-indole composition, and any second anti-inflammatory agent are administered sequentially to the patient, with the anti-inflammatory agent being administered before, after, or both before and after treatment with the bis-indole compound. Sequential administration involves treatment with the anti-inflammatory agent at least on the same day (within 24 hours) of treatment with bis-indole and may involve continued treatment with the anti-inflammatory agent on days that the bis-indole is not administered. Conventional modes of administration and standard dosage regimens of anti-inflammatory agents may be used (see Gilman, A. G. et al [eds.] *The Pharmacological Basis of Therapeutics*, pp. 697–713, 1482, 1489–91 [1980]; *Physicians Desk Reference*, 1986 Edition). For example, indomethacin can be administered orally at a dosage of about 25–50 mg, three times a day. Higher doses can also be used. Alternatively, aspirin (about 1500–2000 mg/day), ibuprofen (about 1200–3200 mg/day), or conventional therapeutic doses of other anti-inflammatory agents can be used. Dosages of anti-inflammatory agents can be titrated to the individual patient.

According to one embodiment of this invention, the patient may receive concurrent treatments with the anti-inflammatory agent and compositions comprising bis-heterocycles, e.g., bis-indoles. For example, local, intralesional, or intravenous injection of bis-indoles is preferred (see Gilman et al., supra at pp. 1290–91). The anti-inflammatory agent should preferably be administered by subcutaneous injection, subcutaneous slow-release implant, or orally.

Alternatively, the patient can receive a composition comprising a combination of one or more bis-indole compounds and an anti-inflammatory agent according to conventional modes of administration of agents which exhibit antibacterial, anticancer, antitumor, or anti-inflammatory activity. These include, for example, parenteral, subcutaneous, intravenous, or intralesional routes of administration.

The compositions used in these therapies can also be in a variety of forms. These include, for example, solid, semisolid, and liquid dosage forms, such as tablets, pills, powders, liquid solutions or suspension, suppositories, injectable and infisible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch, and equivalent carriers and diluents. While effective amounts may vary, as conditions in which compositions are used vary, a minimal dosage required for anti-inflammatory activity is generally between 0.01 and 100 μg of the compound. To provide for the administration of such dosages for the desired therapeutic treatment, new pharmaceutical compositions of the invention will advantageously comprise between about 0.1% and 45%, and especially, 1 and 15% by weight of the total of one or more of the new compounds based on the weight of the total composition including carrier or diluent.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Once improvement of the patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for treating pain in an animal, said method comprising administering an effective amount of a bis-heterocyclic compound, wherein said bis-heterocycle is a bis-indole compound selected from the group consisting of dragmacidins, hamacanthins, homocarbonyltopsentins, nortopsentins, topsentins, and analogs, salts, or derivatives thereof.

2. The method, according to claim 1, wherein said pain is caused by a condition selected from the group consisting of migraine and rhinitis.

3. A method of treatment of an allergic response associated with neurogenic inflammation, wherein said method comprises administering an effective amount of a bis-heterocyclic compound, wherein said bis-heterocyclic compound is a bis-indole compound selected from the groups consisting of dragmacidins, hamacanthins, homocarbonyltopsentins, nortosentins, topsentins, and analogs, salts, or derivatives thereof.

4. A method, according to claim 1, wherein said bis-heterocyclic compound has the following structure:

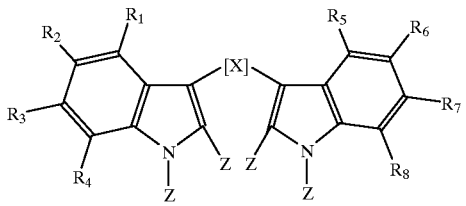

wherein X=an acyclic or a heterocyclic moiety selected from the group consisting of:

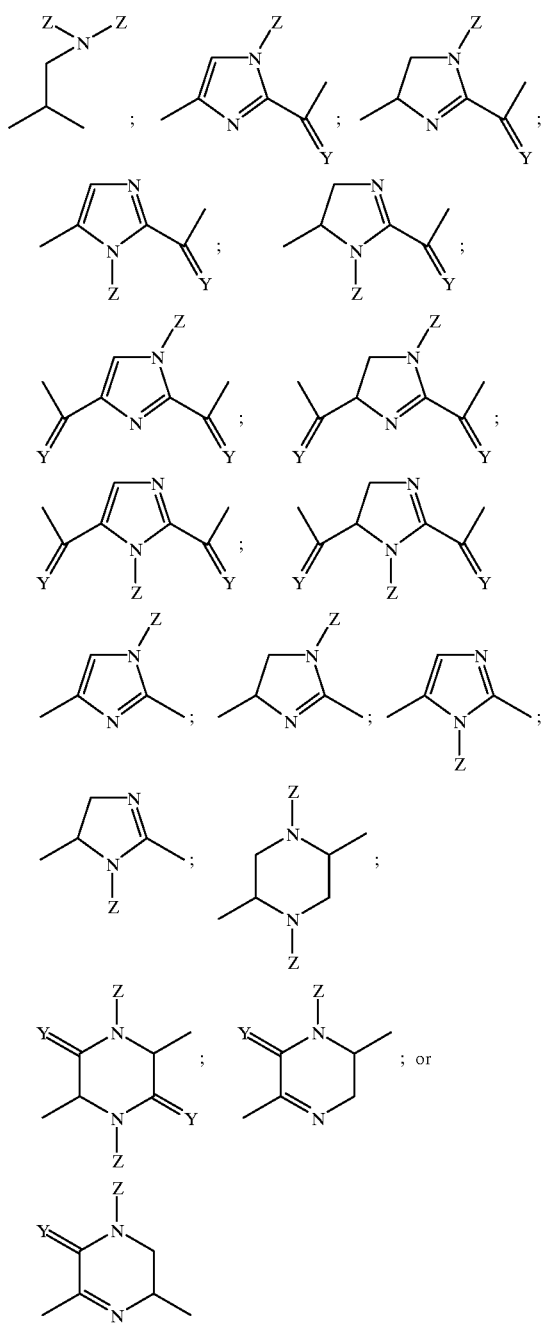

R$_{1-8}$ are the same or different selected from —H, —OH, halogen, —R, —OR, —OCOR, —OA, —NHZ, —NZZ, (wherein the Zs can be the same or different), or NH$_2$;

Y is the single group=O, or the single group=NZ, or two groups, same or different, selected from —H, —OH, —OR, —OCOR, —NHZ, —NZZ (wherein the Zs can be the same or different), or NH$_2$; Z is independently selected from the group consisting of —H, —R, —OH, and —COR; R is C1–8 alkyl, C1–5 alkyl-1-(2-amino imidazole) ethyl, or C1–8 alkoxyl, mesyl, or tosyl; and A is —R-phenyl.

5. The method according to claim 1, wherein said compound has the following structure:

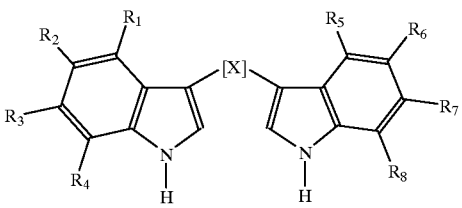

wherein X=

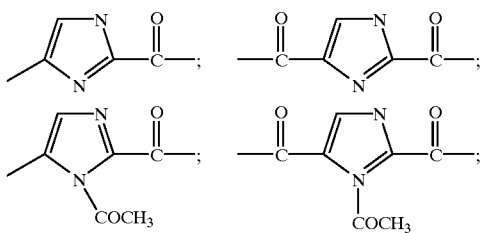

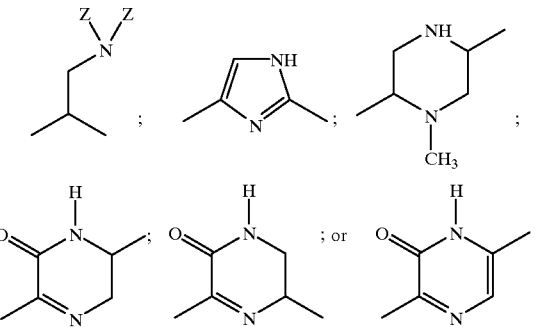

and wherein R$_1$, R$_3$, R$_4$, R$_5$, R$_7$ and R$_8$ are —H while R$_2$ and R$_6$ are independently —H, —OH, halogen, —R, —OR, —OCOR, NH$_2$, NHZ, NZZ (wherein the Zs can be the same or different), or —OA; or R$_1$, R$_2$, R$_4$, R$_5$, R$_6$ and R$_8$ are —H while R$_3$ and R$_7$ are independently —H, —OH, halogen, —R, —OR, —OCOR, NH$_2$, NHZ, NZZ (wherein the Zs can be the same or different), or —OA; Z is independently selected from the group consisting of —H, —R, —OH, and —COR; R is C1–5 alkyl, and A is —R-phenyl; or R$_1$, R$_2$, R$_3$, R$_4$, R$_6$, R$_7$ and R$_8$ are independently —H, —OH, halogen, —R, —OR, —OCOR, or —OA are H and R$_5$ is C1–5 alkyl-1-(2-amino imidazole) ethyl.

6. The method according to claim 1, wherein said compound is topsentin or a salt thereof.

7. The method according to claim 1, wherein said compound is bromotopsentin or a salt thereof.

8. The method according to claim 1, wherein said compound is a hamacanthin.

9. The method according to claim 1, wherein said compound is a dragmacidin.

10. The method according to claim 1, wherein said compound is dragmacidin d.

11. The method according to claim 7, wherein said compound is a bis-indole ethylamine.

12. The method according to claim 1, wherein said compound is administered as a pharmaceutical composition, said pharmaceutical composition comprising one or more compounds of claim 16 and an acceptable pharmaceutical carrier.

13. The method according to claim 3, wherein said bis-heterocyclic compound has the following structure:

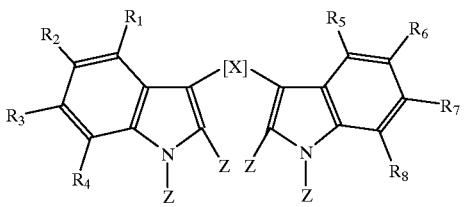

wherein X=an acyclic or a heterocyclic moiety selected from the group consisting of:

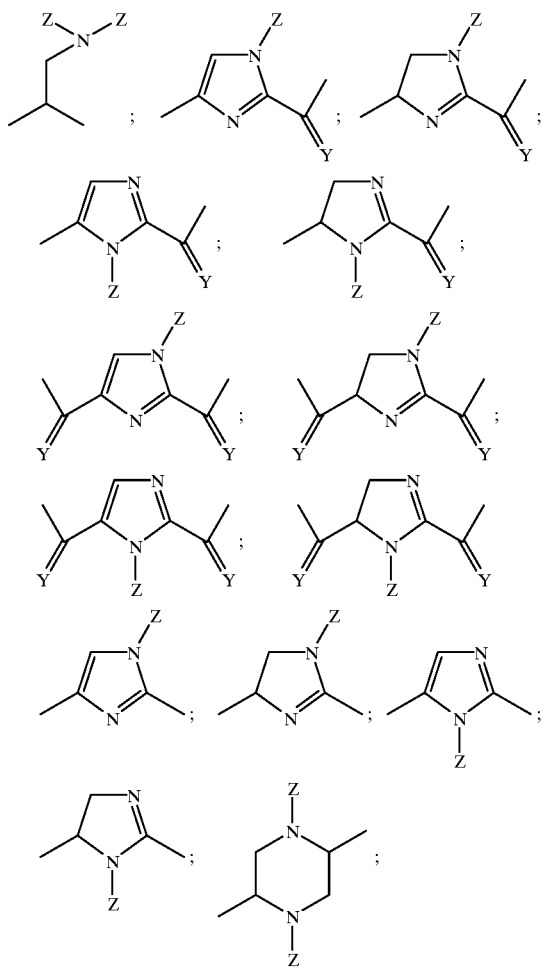

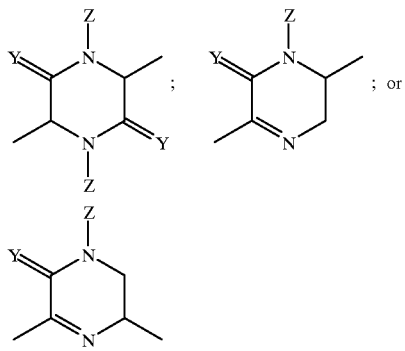

$R^{1-8}$ are the same or different selected from —H, —OH, halogen, —R, —OR, —OCOR, —OA, NHZ, NZZ (wherein the Zs can be the same or different), or $NH_2$; Y is the single group=O, or the single group=NZ, or two groups, same or different, selected from —H, —OH, —OR, —OCOR, NHZ, NZZ (wherein the Zs can be the same or different), or $NH_2$; Z is independently selected from the group consisting of —H, —R, —OH, and —COR;
R is C1–8 alkyl, C1–5 alkyl-1-(2-amino imidazole)ethyl, or C1–8 alkoxyl, mesyl, or tosyl; and A is —R-phenyl.

14. The method according to claim 3, wherein said compound has the following structure:

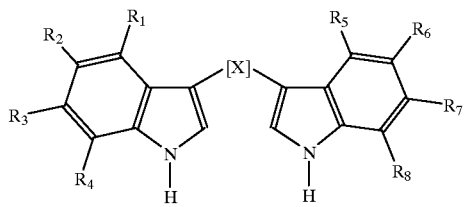

wherein X=

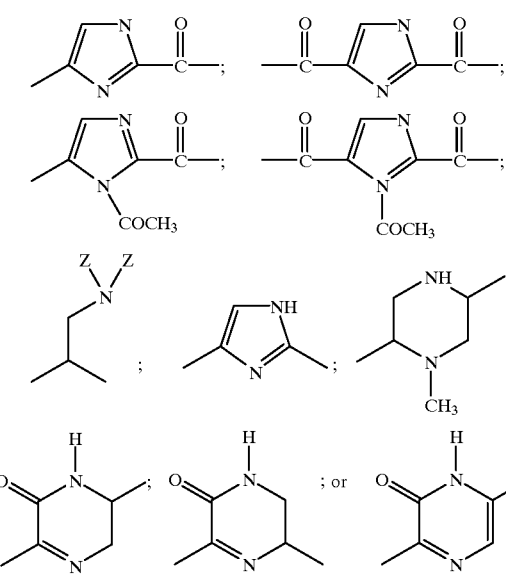

and wherein $R_1$, $R_3$, $R_4$, $R_5$, $R_7$ and $R_8$ are —H while $R_2$ and $R_6$ are independently —H, —OH, halogen, —R, —OR, —OCOR, $NH_2$, NHZ, NZZ (wherein the Zs can be the same or different), or —OA; or $R_1$, $R_2$, $R_4$, $R_5$, $R_6$ and $R_8$ are —H while $R_3$ and $R_7$ are independently —H, —OH, halogen, —R, —OR, —OCOR, $NH_2$, NHZ, NZZ (wherein the Zs can be the same or different), or —OA; Z is independently selected from the group consisting of —H, —R, —OH, and —COR; R is C1–5 alkyl, and A is —R-phenyl; or $R_1$, $R_2$, $R_3$, $R_4$, $R_6$, $R_7$ and $R_8$ are independently —H, —OH, halogen, —R, —OR, —OCOR, or —OA are H and $R_5$ is C1–5 alkyl-1-(2-amino imidazole) ethyl.

15. The method according to claim 3, wherein said compound is topsentin or a salt thereof.

16. The method according to claim 3, wherein said compound is bromotopsentin or a salt thereof.

17. The method according to claim 3, wherein said compound is hamacanthin.

18. The method according to claim 3, wherein said compound is a dragmacidin.

19. The method according to claim 3, wherein said compound is a dragmacidin d.

20. The method according to claim 3, wherein said compound is a bis-indole ethylamine.

21. The method according to claim 3, wherein said compound is administered as a pharmaceutical composition, said pharmaceutical composition comprising one or more compounds of claim 1 and an acceptable pharmaceutical carrier.

* * * * *

UNITED STATES PATENT AND TRADEMARK OFFICE
CERTIFICATE OF CORRECTION

PATENT NO. : 6,090,811
DATED : July 18, 2000
INVENTOR(S) : Jacobs et al.

Page 1 of 1

It is certified that error appears in the above-identified patent and that said Letters Patent is hereby corrected as shown below:

Column 1,
Line 67, "Dragmacidinand" should read -- Dragmacidin and --.

Column 9,
Structure in table "  "

should read -- 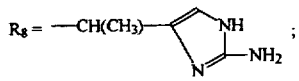 ;

Column 27,
Line 55, "infisible" should read -- infusible --.

Column 31,
Line 5, "claim 7" should read -- claim 1 --.
Line 12, "claim 16" should read -- claim 1 --.

Signed and Sealed this

Twenty-seventh Day of November, 2001

Attest:

NICHOLAS P. GODICI
Attesting Officer   Acting Director of the United States Patent and Trademark Office